United States Patent
McBride et al.

(10) Patent No.: US 7,841,976 B2
(45) Date of Patent: Nov. 30, 2010

(54) HEART ASSIST DEVICE WITH EXPANDABLE IMPELLER PUMP

(75) Inventors: Mark W. McBride, Bellefonte, PA (US); David A. Boger, Glenside, PA (US); Robert L. Campbell, State College, PA (US); Gregory P. Dillon, State College, PA (US); Stephen A. Hambric, State College, PA (US); Robert F. Kunz, State College, PA (US); Boris Leschinsky, Mahwah, NJ (US); Thomas M. Mallison, State College, PA (US); James P. Runt, State College, PA (US); Justin M. Walsh, Spring Mills, PA (US)

(73) Assignees: Thoratec Corporation, Pleasanton, CA (US); The Penn State Research Foundation, University Park, PA (US)

( * ) Notice: Subject to any disclaimer, the term of this patent is extended or adjusted under 35 U.S.C. 154(b) by 773 days.

(21) Appl. No.: 11/728,051

(22) Filed: Mar. 23, 2007

(65) Prior Publication Data

US 2008/0114339 A1    May 15, 2008

Related U.S. Application Data

(60) Provisional application No. 60/785,531, filed on Mar. 23, 2006, provisional application No. 60/785,299, filed on Mar. 23, 2006.

(51) Int. Cl.
*A61M 1/12* (2006.01)
*F04D 29/38* (2006.01)
(52) U.S. Cl. ............... 600/16; 416/412; 416/234; 416/240
(58) Field of Classification Search ............ 600/16–18
See application file for complete search history.

(56) References Cited

U.S. PATENT DOCUMENTS 1,902,418 A    3/1933    Pilgrim (Continued)

FOREIGN PATENT DOCUMENTS

EP    0 364 293    4/1990

(Continued)

OTHER PUBLICATIONS

Schmitz-Rode, Thomas et al., "An Expandable Percutaneous Catheter Pump for Left Ventricular Support", Journal of the American College of Cardiology, Vo. 45, No. 11, 2005, pp. 1856-1861.

(Continued)

*Primary Examiner*—Carl H Layno
*Assistant Examiner*—Luther G Behringer
(74) *Attorney, Agent, or Firm*—Knobbe, Martens, Olson & Bear LLP

(57) ABSTRACT

An impeller includes a hub and at least one blade supported by the hub. The impeller has a stored configuration in which the blade is compressed so that its distal end moves towards the hub, and a deployed configuration in which the blade extends away from the hub. The impeller may be part of a pump for pumping fluids, such as pumping blood within a patient. A blood pump may include a cannula having a proximal portion with a fixed diameter, and a distal portion with an expandable diameter. The impeller may reside in the expandable portion of the cannula. The cannula may have a compressed diameter which allows it to be inserted percutaneously into a patient. Once at a desired location, the expandable portion of the cannula may be expanded and the impeller expanded to the deployed configuration. A flexible drive shaft may extend through the cannula for rotationally driving the impeller within the patient's body.

30 Claims, 22 Drawing Sheets

U.S. PATENT DOCUMENTS

| | | |
|---|---|---|
| 2,356,659 A | 10/1942 | Aguiar |
| 2,649,052 A | 8/1953 | Weyer |
| 2,664,050 A | 12/1953 | Abresch |
| 2,684,035 A | 7/1954 | Kemp |
| 2,789,511 A | 4/1957 | Warren |
| 2,935,068 A | 5/1960 | Donaldson |
| 3,080,824 A | 3/1963 | Boyd et al. |
| 3,510,229 A | 5/1970 | Smith |
| 3,812,812 A | 5/1974 | Hurwitz |
| 3,860,968 A | 1/1975 | Shapiro |
| 4,135,253 A | 1/1979 | Reich et al. |
| 4,149,535 A | 4/1979 | Volder |
| 4,304,524 A | 12/1981 | Coxon et al. |
| 4,458,366 A | 7/1984 | MacGregor |
| 4,540,402 A | 9/1985 | Aigner |
| 4,589,822 A | 5/1986 | Clausen et al. |
| 4,625,712 A | 12/1986 | Wampler |
| 4,686,982 A | 8/1987 | Nash |
| 4,753,221 A | 6/1988 | Kensey |
| 4,769,006 A | 9/1988 | Papantonakos |
| 4,846,152 A | 7/1989 | Wampler et al. |
| 4,900,227 A | 2/1990 | Trouplin et al. |
| 4,902,272 A | 2/1990 | Milder et al. |
| 4,908,012 A | 3/1990 | Moise et al. |
| 4,919,647 A | 4/1990 | Nash |
| 4,944,722 A | 7/1990 | Carriker et al. |
| 4,957,504 A | 9/1990 | Chardack |
| 4,964,864 A | 10/1990 | Summers et al. |
| 4,985,014 A | 1/1991 | Orejola |
| 4,994,017 A | 2/1991 | Yozu |
| 5,049,134 A | 9/1991 | Golding et al. |
| 5,089,016 A | 2/1992 | Millner et al. |
| 5,092,844 A | 3/1992 | Schwartz et al. |
| 5,098,256 A | 3/1992 | Smith |
| 5,112,200 A | 5/1992 | Isaacson et al. |
| 5,112,349 A | 5/1992 | Summers et al. |
| 5,129,883 A | 7/1992 | Black |
| 5,171,212 A | 12/1992 | Buck et al. |
| 5,201,679 A | 4/1993 | Velte, Jr. et al. |
| 5,211,546 A | 5/1993 | Isaacson et al. |
| 5,290,227 A | 3/1994 | Pasque |
| 5,346,458 A | 9/1994 | Affeld |
| 5,360,317 A | 11/1994 | Clausen et al. |
| 5,376,114 A | 12/1994 | Jarvik |
| 5,437,541 A | 8/1995 | Vainrub et al. |
| 5,458,459 A | 10/1995 | Hubbard et al. |
| 5,505,701 A | 4/1996 | de Lomana |
| 5,527,159 A | 6/1996 | Bozeman, Jr. et al. |
| 5,533,957 A | 7/1996 | Aldea |
| 5,588,812 A | 12/1996 | Taylor et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,707,218 A | 1/1998 | Maher et al. |
| 5,722,930 A | 3/1998 | Larson et al. |
| 5,746,709 A | 5/1998 | Rom et al. |
| 5,749,855 A | 5/1998 | Reitan et al. |
| 5,755,784 A | 5/1998 | Jarvik |
| 5,824,070 A | 10/1998 | Jarvik |
| 5,851,174 A | 12/1998 | Jarvik et al. |
| 5,868,703 A | 2/1999 | Bertolero |
| 5,888,242 A | 3/1999 | Antaki et al. |
| 5,911,685 A | 6/1999 | Siess et al. |
| 5,921,913 A | 7/1999 | Siess |
| 5,941,813 A | 8/1999 | Sievers et al. |
| 5,951,263 A | 9/1999 | Taylor et al. |
| 5,964,694 A | 10/1999 | Siess et al. |
| 6,007,479 A | 12/1999 | Rottenberg et al. |
| 6,058,593 A | 5/2000 | Siess |
| 6,086,527 A | 7/2000 | Talpade |
| 6,123,659 A | 9/2000 | le Blanc et al. |
| 6,132,363 A | 10/2000 | Freed et al. |
| 6,135,943 A | 10/2000 | Yu et al. |
| 6,139,487 A | 10/2000 | Siess |
| 6,176,822 B1 | 1/2001 | Nix et al. |
| 6,176,848 B1 | 1/2001 | Rau et al. |
| 6,190,304 B1 | 2/2001 | Downey et al. |
| 6,200,260 B1 | 3/2001 | Bolling |
| 6,227,797 B1 | 5/2001 | Watterson et al. |
| 6,245,007 B1 | 6/2001 | Bedingham et al. |
| 6,247,892 B1 | 6/2001 | Kazatchkov et al. |
| 6,254,359 B1 | 7/2001 | Aber |
| 6,295,877 B1 | 10/2001 | Aboul-Hosn et al. |
| 6,387,037 B1 | 5/2002 | Bolling et al. |
| 6,422,990 B1 | 7/2002 | Prem |
| 6,425,007 B1 | 7/2002 | Messinger |
| 6,428,464 B1 | 8/2002 | Bolling |
| 6,447,441 B1 | 9/2002 | Yu et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | deBlanc et al. |
| 6,609,883 B2 | 8/2003 | Woodard et al. |
| 6,610,004 B2 | 8/2003 | Viole et al. |
| 6,623,420 B2 | 9/2003 | Reich et al. |
| 6,692,318 B2 | 2/2004 | McBride |
| 6,716,189 B1 | 4/2004 | Jarvik et al. |
| 6,749,598 B1 | 6/2004 | Keren et al. |
| 6,776,578 B2 | 8/2004 | Belady |
| 6,783,328 B2 | 8/2004 | Lucke et al. |
| 6,790,171 B1 | 9/2004 | Grundeman et al. |
| 6,794,789 B2 | 9/2004 | Siess et al. |
| 6,817,836 B2 | 11/2004 | Nose et al. |
| 6,860,713 B2 | 3/2005 | Hoover |
| 6,866,625 B1 | 3/2005 | Avre et al. |
| 6,942,611 B2 | 9/2005 | Siess |
| 6,949,066 B2 | 9/2005 | Bearnson et al. |
| 6,966,748 B2 | 11/2005 | Woodard et al. |
| 6,974,436 B1 | 12/2005 | Aboul-Hosn et al. |
| 6,981,942 B2 | 1/2006 | Khaw et al. |
| 6,984,392 B2 | 1/2006 | Bechert et al. |
| 7,010,954 B2 | 3/2006 | Siess et al. |
| 7,011,620 B1 | 3/2006 | Siess |
| 7,022,100 B1 | 4/2006 | Aboul-Hosn et al. |
| 7,027,875 B2 | 4/2006 | Siess et al. |
| 7,070,555 B2 | 7/2006 | Siess |
| 7,150,711 B2 | 12/2006 | Nusser et al. |
| 7,160,243 B2 | 1/2007 | Medvedev |
| 7,175,588 B2 | 2/2007 | Morello |
| 7,284,956 B2 | 10/2007 | Nose et al. |
| 7,331,921 B2 | 2/2008 | Viole et al. |
| 7,393,181 B2 | 7/2008 | McBride |
| 7,491,163 B2 | 2/2009 | Viole et al. |
| 7,731,675 B2 | 6/2010 | Aboul-Hosn et al. |
| 2002/0169413 A1 | 11/2002 | Keren et al. |
| 2003/0135086 A1 | 7/2003 | Khaw et al. |
| 2003/0231959 A1 | 12/2003 | Snider |
| 2004/0101406 A1 | 5/2004 | Hoover |
| 2005/0095124 A1 | 5/2005 | Arnold et al. |
| 2006/0018943 A1 | 1/2006 | Bechert et al. |
| 2006/0058869 A1 | 3/2006 | Olson et al. |
| 2007/0203442 A1 | 8/2007 | Bechert et al. |
| 2008/0103591 A1 | 5/2008 | Siess |
| 2009/0060743 A1 | 3/2009 | McBride et al. |
| 2009/0093764 A1 | 4/2009 | Pfeffer et al. |
| 2009/0093765 A1 | 4/2009 | Glenn |
| 2009/0093796 A1 | 4/2009 | Pfeffer et al. |
| 2009/0171137 A1 | 7/2009 | Farnan et al. |
| 2010/0016960 A1 | 1/2010 | Bolling |

FOREIGN PATENT DOCUMENTS

| | | |
|---|---|---|
| FR | 2267800 | 4/1974 |
| JP | H08-196624 | 8/1996 |
| WO | WO-94/05347 | 3/1994 |
| WO | WO 97/15228 | 5/1997 |
| WO | WO 99/37352 | 7/1999 |
| WO | WO-99/44651 A1 | 9/1999 |
| WO | WO 99/59652 | 11/1999 |
| WO | WO 00/12148 | 3/2000 |
| WO | WO 01/24867 | 4/2001 |
| WO | WO 03/048582 | 6/2003 |
| WO | WO-03/103745 | 12/2003 |
| WO | WO-2006/051023 A1 | 5/2006 |

OTHER PUBLICATIONS

International Search Report received in PCT Application No. PCT/US2005/33416, mailed Dec. 11, 2006, 4 pages.

International Preliminary Report on Patentability and Written Opinion of the International Searching Authority received in PCT Application No. PCT/US2005/033416, mailed Mar. 20, 2007, 7 pages.

International Search Report received in PCT Application No. PCT/US2007/07313, mailed Mar. 4, 2008, 3 pages.

International Preliminary Report on Patentability and Written Opinion of the International Searching Authority received in PCT Application No. PCT/US2007/007313, mailed Sep. 23, 2008, 6 pages.

U.S. Appl. No. 12/565,651 filed Sep. 23, 2009.

U.S. Appl. No. 12/772,810 filed on May 3, 2010.

Copending U.S. Appl. No. 12/829,359 filed on Jul. 1, 2010.

Copending U.S. Appl. No. 12/772,810 filed on May 3, 2010.

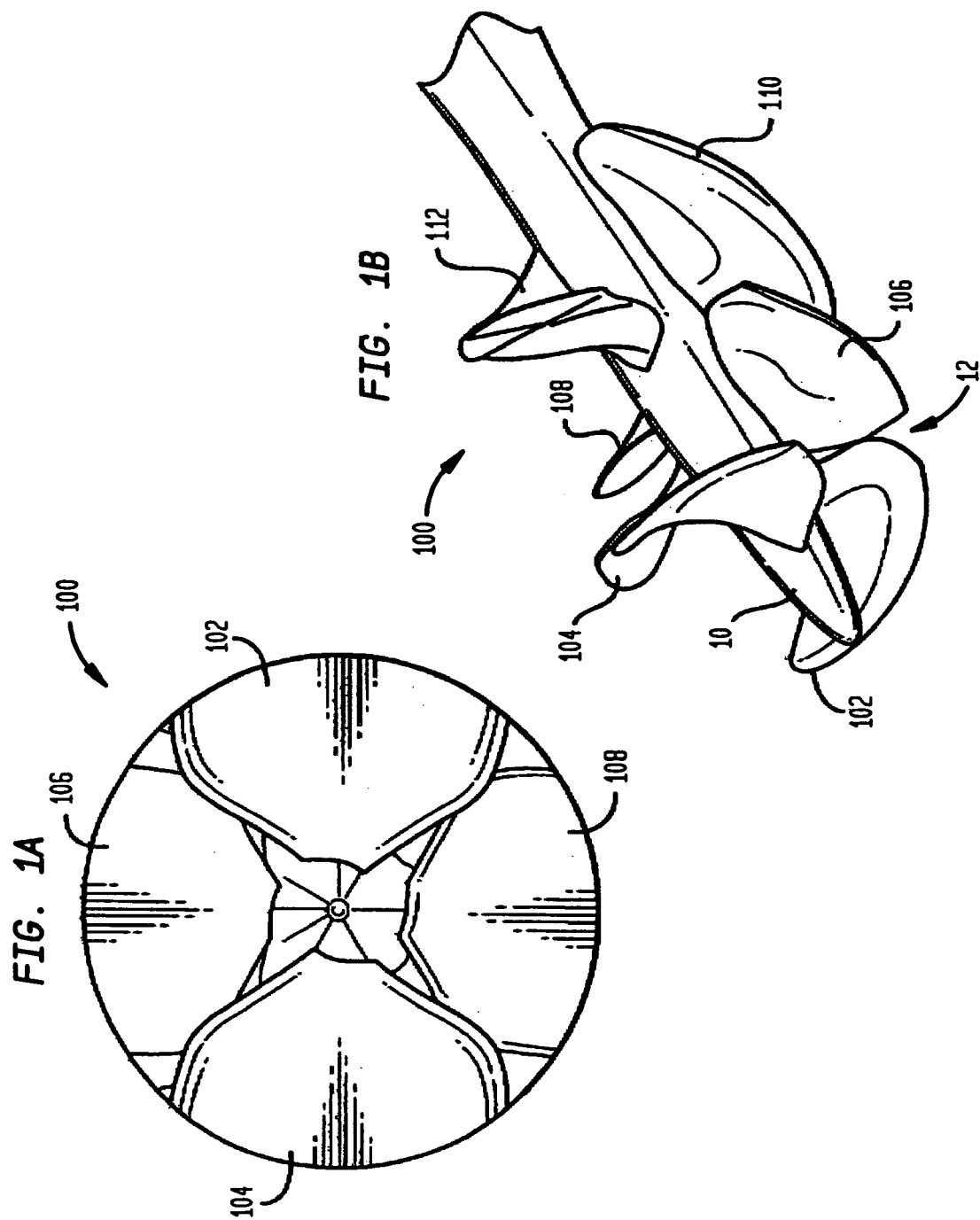

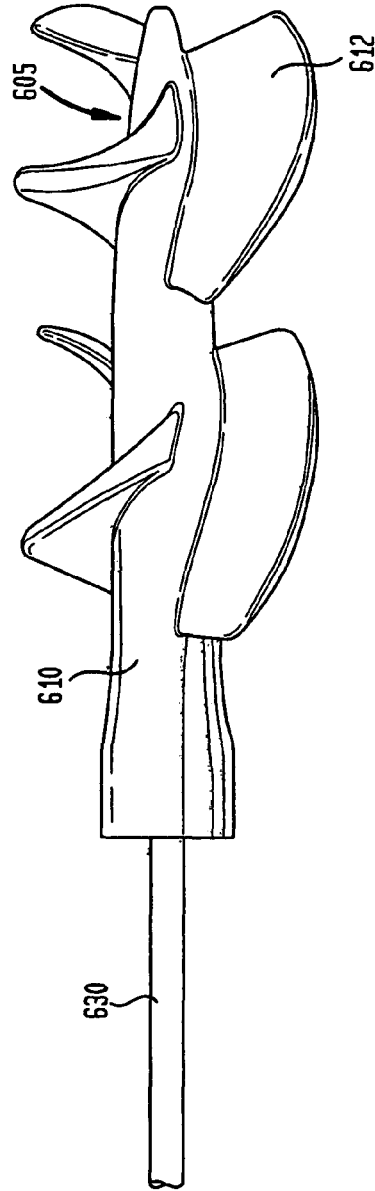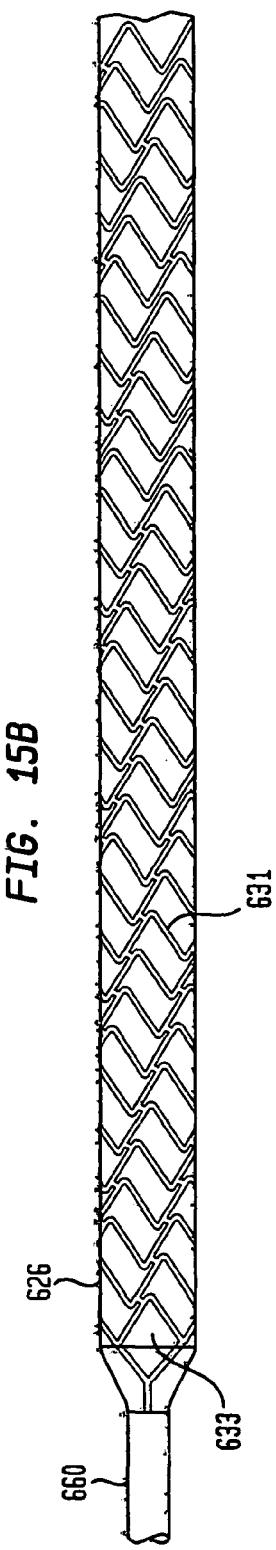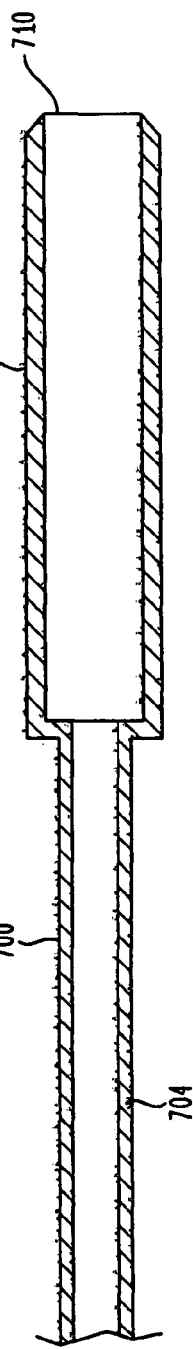

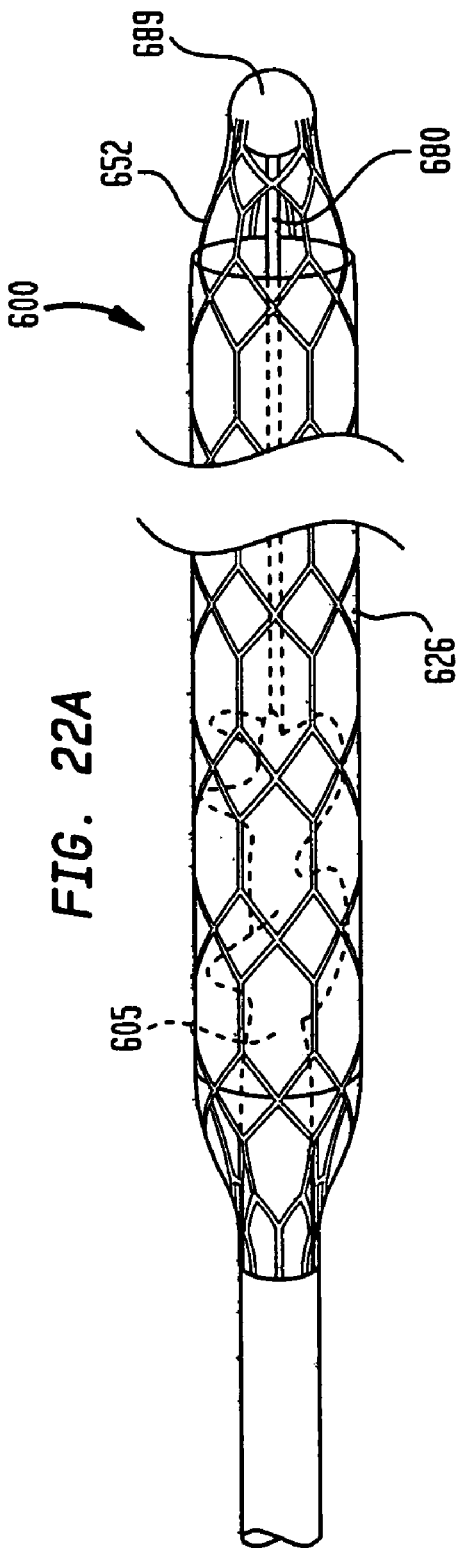
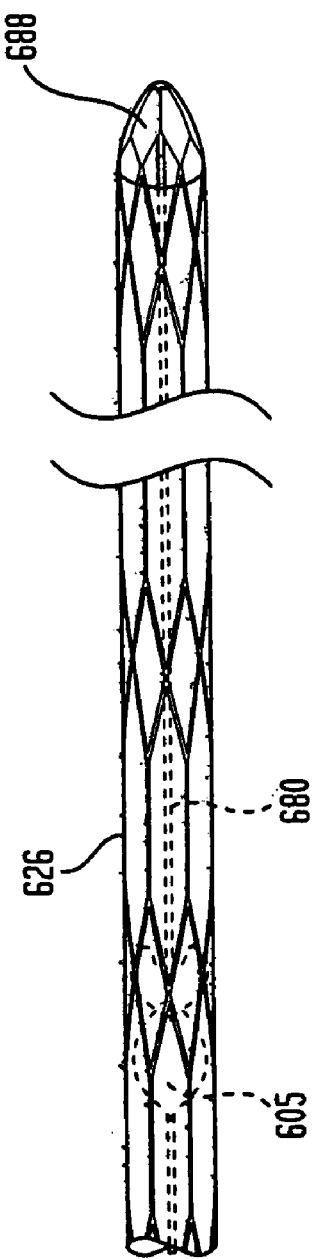
FIG. 22A
FIG. 22B

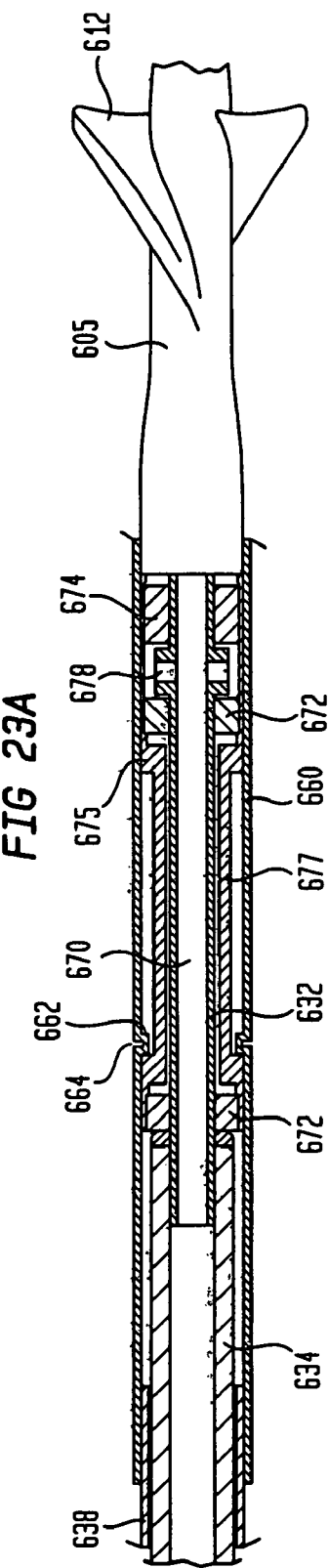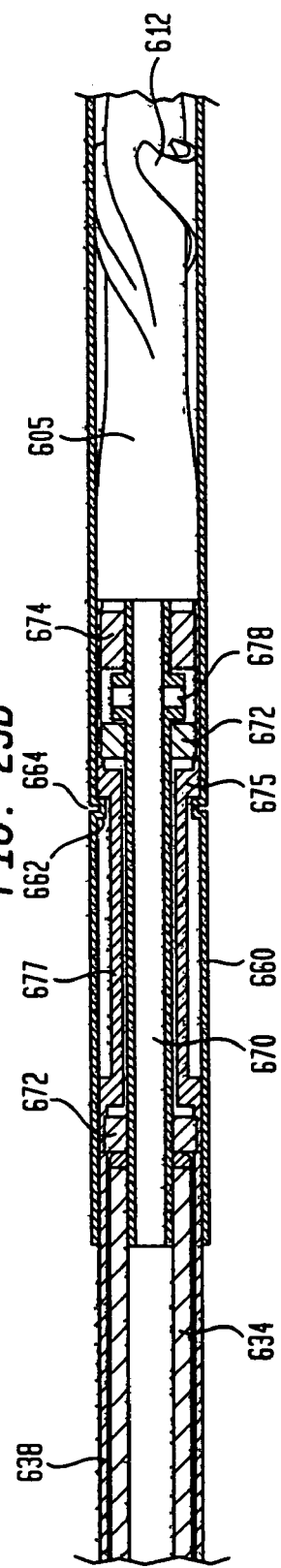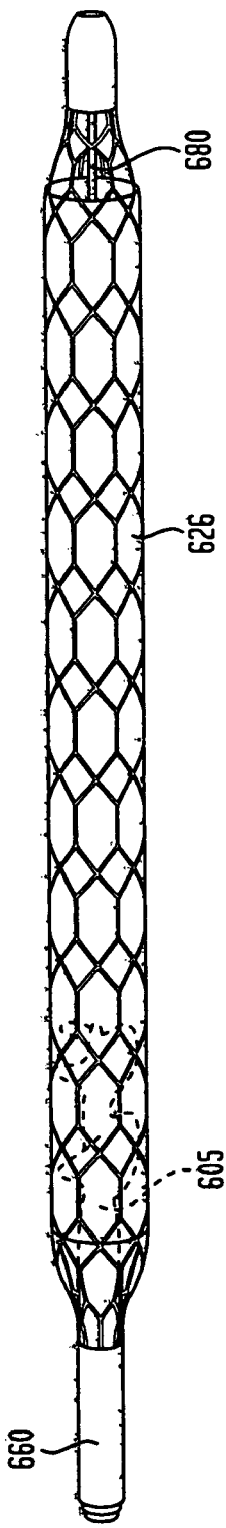

HEART ASSIST DEVICE WITH EXPANDABLE IMPELLER PUMP

CROSS-REFERENCE TO RELATED APPLICATIONS

This application claims the benefit of the filing dates of U.S. Provisional Application Nos. 60/785,299, filed on Mar. 23, 2006 and 60/785,531, filed on Mar. 23, 2006, the disclosures of which are hereby incorporated by reference herein. Further, the entire disclosures of U.S. Provisional Application No. 60/610,938, filed on Sep. 17, 2004, and U.S. Patent Application Ser. No. 11/227,277, now U.S. Pat. No. 7,393,181, filed on Sep. 15, 2005, are hereby incorporated by reference herein.

FIELD OF THE INVENTION

The present invention relates to fluid pumping impellers, more particularly to expandable fluid pumping impellers. Still more particularly, the present invention relates to blood pumps such as left or right ventricular assist devices with an expandable impeller for treatment of heart disease.

BACKGROUND OF THE INVENTION

Heart disease is a major problem in society, and claims many lives per year. After a heart attack, only a small number of patients can be treated successfully and non-invasively using medicines, such as pharmaceuticals. However, with sufficient mechanical assistance to the heart function, a majority of patients may recover from a heart attack, including even those with cardiogenic shock.

In a conventional approach, a blood pump having a fixed cross-section is surgically inserted within the left ventricle of the heart and the aortic arch to assist the heart in its function. Surgical placement is required, since it is presently impractical or impossible to insert a pump of the size needed for sustaining adequate blood flow percutaneously. The object of the surgically inserted pump is to reduce the load on the heart muscle for a period of time, which may be as long as a week, allowing the affected heart muscle to recover while healing in a resting mode.

Surgical insertion, however, can cause additional serious stresses in heart failure cases. Percutaneous insertion of a left ventricular assist device ("LVAD") therefore is desired. However, the conventional fixed cross-sectional diameter of such an LVAD cannot fit through the femoral artery of the leg in which it must travel to be positioned into the left ventricle. The maximum diameter of such a fixed diameter LVAD would have to be limited to approximately four millimeters for practical percutaneous insertion. This would limit the maximum pumped blood flow rate to approximately two liters per minute, approximately one-half the desired sustaining blood flow value for many cases. While the pumping rate can be increased by increasing the diameter of the device, particularly the diameter of the impeller, the size of the femoral artery is a limiting factor for percutaneous insertion. Hence, there is an urgent need for a pumping device that can be implanted through percutaneous insertion and yet provide the sustaining blood flow rates that conventional surgically implanted pumps provide.

SUMMARY OF THE INVENTION

The present invention may be used as an LVAD, a right ventricular assist device ("RVAD") or in other situations that may benefit from a blood pump that is expandable in situ after being inserted into the body of a patient. The blood pump has an impeller design that allows compression and expansion of the impeller at the discretion of the operator. This compression/expansion feature allows for increased blood flow through the blood pump due to an increase, by expansion, of the impeller size, thereby producing a blood flow capable of sustaining human life without the need for significant contribution by the heart muscle. The blood flow provided is typically at least 4 liters per minute of blood, the flow that is usually sufficient to sustain life.

The difference in using the blood pump as an LVAD as opposed to an RVAD is the location of the pump in the patient and the flow direction of blood through the pump.

BRIEF DESCRIPTION OF THE DRAWINGS

FIG. 1A is an end view of an embodiment of an impeller having three rows of blades (blade rows);

FIG. 1B is a perspective view of the impeller of FIG. 1A;

FIG. 15A is a side elevational view of the impeller portion of the blood pump of FIG. 14;

FIG. 15B is a side elevational view of a cannula in which the impeller of the blood pump of FIG. 14 operates;

FIG. 15C is a partial longitudinal cross-sectional view of the retainer sheath for use with the blood pump of FIG. 14;

FIGS. 22A and 22B are longitudinal highly schematic views of the blood pump of the present invention in the deployed and stored configurations, respectively, showing system components;

FIG. 23A is a longitudinal cross-sectional view of the blood pump of FIG. 14 in its deployed configuration;

FIG. 23B is a longitudinal cross-sectional view of the blood pump of FIG. 14 in its retracted position;

FIG. 23C is a side elevational view of a cannula in which the impeller of the blood pump of FIG. 14 operates;

DETAILED DESCRIPTION

Figure 2A:
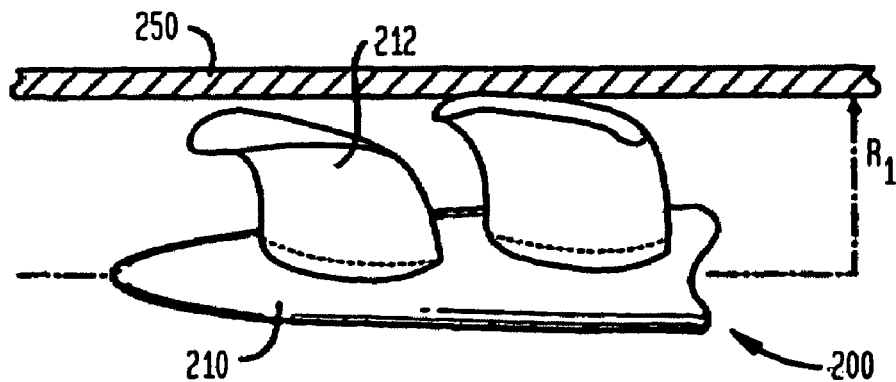
FIG. 2A is a highly schematic side elevational view of an embodiment of an impeller according to the present invention in its deployed configuration.

An impeller according to embodiments of the present invention includes a hub, and at least one blade supported by the hub. The impeller may have a deployed configuration in which the blade extends away from the hub, and a stored configuration in which the impeller is radially compressed, for example by folding the blade towards the hub.

In some embodiments, the outer edge of a blade may have a winglet. The impeller also may have a trench or indentation proximate to a blade root to facilitate folding of the blade and/or to reduce shear stresses in the fluid flow induced by rotation of the impeller.

Some embodiments of the present invention include impellers that do not radially compress, but retain a generally constant configuration. Impellers according to the present invention may be used in various applications, including improved blood pumps.

Blade Rows

Impellers according to embodiments of the present invention may include a plurality of blades which may be arranged in one or more blade rows positioned along the impeller hub. FIGS. 1A and 1B illustrate end and side views, respectively, of an impeller 100. The impeller includes a hub 10, and a plurality of blades 12 arranged in three blade rows. The first blade row includes blades 102 and 104, the second blade row includes blades 106 and 108, and the third blade row includes blades 110 and 112.

The provision of a plurality of blade rows facilitates the folding of the blades into a stored configuration as compared to the difficulty of folding a single helical blade extending a similar distance along the hub. Each blade row may include the same number of blades, for example, one to three blades.

Alternatively, the number of blades in each blade row may differ. For embodiments in which there are more than two blade rows, the number of blades in at least one blade row may differ from the number of blades in other blade rows. The provision of a plurality of blade rows facilitates the achievement of larger values of fluid head or pressure rise than a single blade row, while allowing the impeller to be radially compressed into a stored configuration.

One approach to impeller design provides an impeller having a long helical blade exhibiting a significant degree of wrap around the central hub. However, the three-dimensional shape of long helical blades limits the degree to which they can be folded without breaking or permanently deforming. By dividing a single helical blade into a plurality (two, three or possibly more) of individual blades, arranged in blade rows, the blades in each row exhibit less wrap around the hub. Therefore, the individual blades may have an essentially two-dimensional shape which allows easier deformation during the storage process. The combination of two or more blade rows can produce the same flow and pressure as a single helical blade of similar axial extent. For example, individual blades may have a height-to-chord length ratio in the range of about 0.5-1.5, and a plurality of blade rows of such more easily folded blades may combine to provide a similar hydraulic efficiency as a longer serpentine blade. Further, in blood pumping applications, the use of a long serpentine blade may lead to separated flows, leading to thrombosis, which can be avoided using multiple blade rows.

Hence, impellers according to some embodiments of the present invention may have multiple separate sets of blades, rather than a long, continuous helical blade. A continuous long helical blade is difficult to fold up against the hub, and by splitting a long blade into two or three shorter sections, the blade can be more easily folded into a cylindrical volume or space and subsequently deployed when desired.

An impeller according to the present invention may include at least two blades arranged about the circumference of the hub in a first blade row. The at least two blades may be positioned approximately $360/N°$ apart from one another about the circumference of the hub, where N represents the total number of blades in the first blade row. The impeller alternatively may include a plurality of blades arranged in at least two blade rows, with each blade row including at least two blades. The at least two blades in the first row of blades may be positioned $360/N_1°$ apart from one another about the circumference of the hub and the at least two blades in the second row of blades may be positioned $360/N_2°$ apart from one another about the circumference of the hub, where $N_1$ represents the total number of blades in the first row and $N_2$ represents the total number of blades in the second row. $N_1$ and $N_2$ may be the same or different. The first and second rows of blades may be circumferentially offset relative to one another by $360/2N_1°$.

Preferably, the number of blade rows is two or three. The blade rows may be interleaved (overlapping along the axial direction), which can increase performance but may increase the diameter of the impeller in the stored configuration. If blades are interleaved, they will tend to fold on each other in the stored configuration, increasing the stored diameter of the impeller.

To minimize the stored diameter of the impeller, for example for blood pumping applications, the blade rows are preferably spaced apart along the hub, proximate to each other but not interleaved. For example, the spacing between blade rows may be less than the axial extent of each blade row along the hub axis. A larger blade row spacing allows shear wakes to decay between blade rows, but lengthens the impeller, making it more difficult to move the impeller along a curved path, such as along blood vessels to a desired location within a patient.

Blade rows may also be clocked relative to each other, the clocking being an angular displacement between corresponding blades of each blade row, and in particular, an angular displacement between the trailing edge of a blade in one row and the leading edge of the corresponding blade in the next row. For example, an impeller may have at least a first blade row and a second blade row, the first and second blade rows including a similar number of blades. The blades of the first blade row may be angularly offset (clocked) relative to the corresponding blades of the second blade row. In blood pumping applications, the angular offset can be adjusted to reduce hemolysis. Blades may be clocked so that the leading edge of a following blade does not reside in the wake from a leading blade, and the clocking may be clockwise or counterclockwise to achieve this. Blade rows may be clocked relative to each other to avoid tandem blade effects, where the following blade resides wholly in the boundary layer or wake of the leading blade, so as to reduce shear stresses.

Other Blade Parameters

The amount of lean or tilt of the blades may be adjusted according to the blade stiffness. The blade lean may be a forward lean (toward the pressure face) of between about 30° and about 60°. A forward lean blade tends to deform so as to increase the angle of incidence of the fluid at the tip, and thus increase the load on the blades. Conventional propellers use a backward lean blade which tends to unload the blade tip under structural deflection. Hence, the use of a forward lean is unusual. Forward lean of flexible blades may be used to minimize the gap between a blade tip and the inside surface of a conduit in which the impeller operates. A backward lean may make it more difficult to control the size of the gap.

The twist pitch angles of the blades also may be variable, for example for impeller operation in a conduit. The blade deviation angle may be in the range about 15 to 30 degrees to assist impeller operation at low Reynolds number operation (for example, less than 50,000 for the blade tip chord) within a conduit, hence reducing hemolysis in blood pump applications. The pitch at the tip, measured relative to a circumferential direction, can be appreciably less than the pitch at the root, to match slower fluid flow within a boundary layer near the inside surface of the conduit. Hence, the blade of an improved impeller for operation within a laminar flow profile within a cannula has a blade twist, the pitch being approximately matched to the flow profile, the blade tip having a smaller pitch angle than the blade root. The blade may have a slightly humped appearance in a region of relatively rapid change in blade pitch.

For external flow applications (not in a conduit), the twist in the blade pitch may be in the opposite direction as any boundary layer will tend to be closer to the hub.

The root of a serpentine blade exhibits a geometric characteristic known as camber, the curvature of the airfoil section if laid out on a flat surface. By dividing a single long blade into two or more sections, the camber of the resulting partial sections can be limited, for example to values of less than 10%, for example 5%. In the latter case, the deviation of any section from a straight line will be on the order of five percent of the section chord length. For example, a serpentine blade having a camber of 15% may be divided into three sections, each of which will be substantially linear and more easily folded. The result would be an impeller having three blades, arranged in three blade rows, with performance similar to that of the serpentine blade. The wrap angle (from the leading edge to the trailing edge) can be limited to a maximum of about 30 degrees. Hence, blade rows may each contain substantially two-dimensional blades (compared with a single serpentine blade of similar pumping efficiency), the blades more readily folding against the hub than would a serpentine blade.

The modulus of the blades may be lower for deforming the blades to the stored configuration of the impeller, which may correspond, for example, to strains of 100%-200%. In representative examples, the modulus for the larger blade deformations in the stored configuration may be about ten times less than the modulus for operational stresses. For example, the impeller may include blades formed from a material having a flexural modulus of about 10,000 psi for operational stresses and about 1,000 psi for storage deformations.

FIG. 2A shows an impeller 200 in a deployed configuration, the impeller including a hub 210 and a plurality of blades 212. Impeller 200 has a radius $R_1$ in the deployed configuration, as measured from the central longitudinal axis of hub 210 to the outermost blade tip. The deployed diameter is twice the deployed radius, and is the diameter of a circle described by the blade tip as impeller 200 rotates around the longitudinal axis of hub 210. Also shown is a wall of a conduit 250 through which fluid flows relative to impeller 200. Impeller 200 may be used as an axial pump, to pump fluid through conduit 250. Alternatively, impeller 200 may be used as a motive force provider for a vehicle. For example, the impeller may power a boat, such as a jet-boat, or other water craft. In such example, conduit 250 could be a tube immersed in the water surrounding the vehicle, or there may be no conduit at all.

Figure 2B:
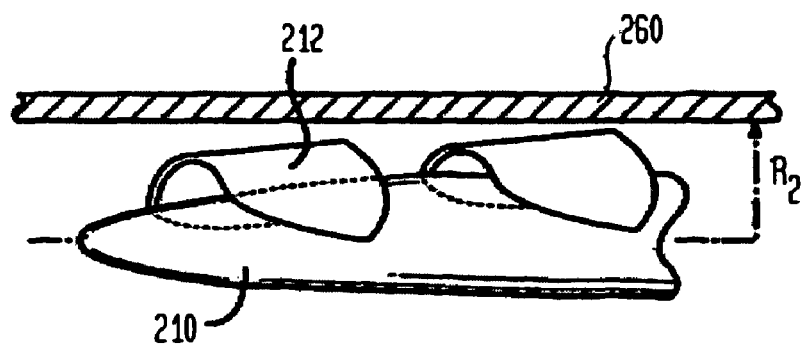
FIG. 2B is a highly schematic side elevational view of the impeller of FIG. 2A in its stored configuration.

FIG. 2B shows impeller 200 in a stored configuration, with blades 212 folded or otherwise deformed towards hub 210 and held in this stored configuration by a storage housing 260. The radius $R_2$ of storage housing 260, which in this case defines the stored diameter of impeller 200, is appreciably less than the radius $R_1$ of the deployed impeller shown in FIG. 2A. A deformed impeller blade 212 may contact the inside surface of storage housing 260 at one or more locations.

In embodiments of the present invention, the flexible blades 212 of impeller 200 can be folded or otherwise radially compressed such that the maximum diameter of the impeller in the stored configuration is approximately half, or less than half, the diameter of the impeller in the deployed configuration. Referring to FIGS. 2A and 2B, this corresponds to $R2 \approx \leq (R1/2)$. A ratio of $R2 \approx \leq (R1/2)$ is useful for blood pump applications, allowing a blood pump to deploy to a diameter of between about 6 millimeters and about 7 millimeters within a human body, while being non-surgically inserted with a diameter of between about 3 millimeters and about 4 millimeters. Other diameter ratios are useful for other applications.

Impeller Deployment within a Conduit

Figure 3:
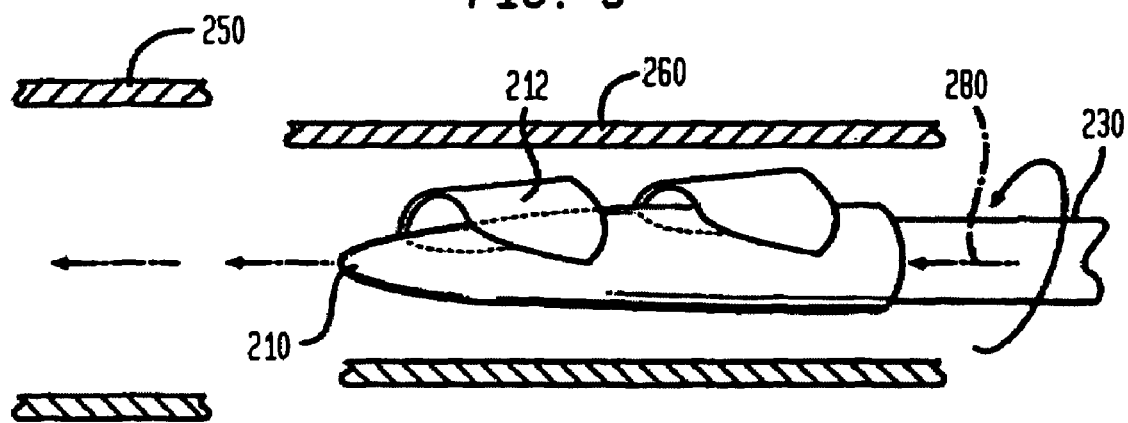
FIG. 3 is a highly schematic side elevational view schematically illustrating the deployment of the impeller of FIG. 2A.

FIG. 3 is a schematic view illustrating the deployment of impeller 200. Impeller 200 has hub 210 and blades 212, and is retained in the stored configuration by storage housing 260. Storage housing 260 may be a tube in which impeller 200 is stored prior to deployment. A drive shaft 230 is used to rotate impeller 200. The figure also shows an optional guide wire 280 within rotating drive shaft 230 which can be used to position impeller 200 at a desired location. The rotation of drive shaft 230 may also assist in deploying impeller 200, for example through twisting the impeller out of storage housing 260 if the inner surface of the storage housing has a threaded texture.

On the left of the figure, conduit 250 is shown into which impeller 200 is deployed for operation in its larger deployed configuration. Conduit 250 may represent any structure through which a fluid may flow relative to impeller 200, such as a tube, catheter, cannula, or body vessel such as a blood vessel.

Impeller 200 contained within its storage housing 260 may be deployed within a conduit, such as a utility pipe (water, gas, sewage, and the like), body vessel, (such as a blood vessel), portion of a thrust unit for a vehicle, or other structure through which a fluid may flow. The impeller can be conveyed to a desired location within the conduit in a stored configuration, and then deployed to the deployed configuration. Impeller 200 can be deployed by urging the impeller axially out of storage housing 260, for example using drive shaft 230 attached to the impeller. The impeller then unfolds into the deployed configuration using the stored potential energy of blades 212 in the stored configuration.

The stored configuration facilitates conveyance of impeller 200 to the desired location, enabling it to be passed through openings which are smaller than the diameter of the impeller in the deployed configuration. To remove impeller 200 from the conduit after use, the impeller may be radially compressed back into the stored configuration, for example by urging the impeller back into storage housing 260, such as by re-folding flexible blades 212 against hub 210. The stored impeller may then be removed from the use location through an access hole having a dimension less than the diameter of the impeller in the deployed configuration. Hence, impeller 200 can be inserted in the stored configuration through a relatively small entrance hole into a conduit 250 of larger diameter.

Although storage housing 260 is described above as a tube from which impeller 200 may be deployed by axial movement out of the storage housing, that need not be the case. Rather, storage housing 260 may itself be expandable or have an expandable portion, as described below. Expansion of storage housing 260 would allow impeller 200 to deploy, such that the impeller would not need to be pushed axially out of the storage housing to achieve the deployed configuration. Thus, with reference to FIG. 3, conduit 250 may represent storage housing 260 in an expanded condition.

Winglets

Impellers according to the present invention may include at least one blade having a winglet. In some embodiments, all blades within a blade row may include such a winglet; other blades in the impeller may or may not include a winglet. A winglet may improve hydrodynamic performance of the impeller in the operating state, and may also reduce shear stresses that exist within the fluid being pumped. As a result, when the fluid being pumped includes biological structures such as cells, the degradation of such structures by the pumping action may be reduced.

An impeller blade typically has a pair of opposed faces: a pressure face inducing relative motion of the fluid through pressure as the blade rotates through the fluid; and a suction face inducing fluid motion by suction. Typically, the pressure and suction faces are not planar, but rather are curved in the same general direction to define an airfoil shape. The blade also has a leading edge cutting through the fluid as the blade rotates, a trailing edge, and an outer edge (which may also be referred to as a blade tip or distal end of the blade). A winglet may extend in the direction of motion of the impeller (from the pressure face of the blade), in the direction opposite the direction of motion (from the suction face of the blade), or in both directions.

Figure 4A:
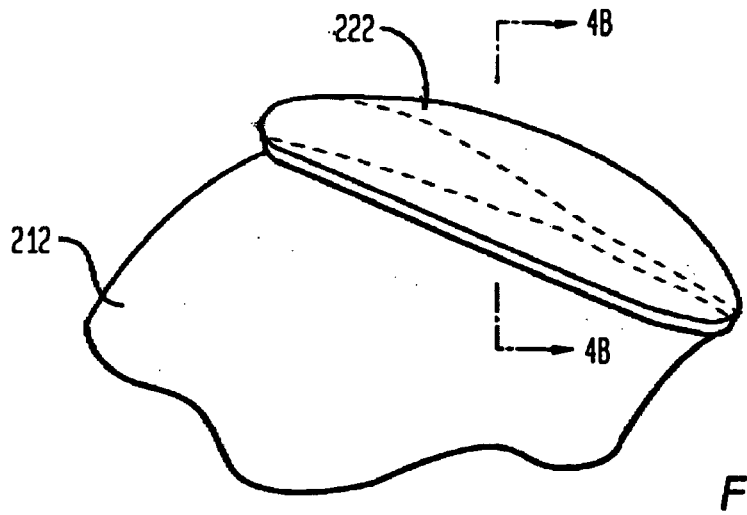
FIG. 4A is an enlarged perspective view of a portion of a blade having an embodiment of a winglet.
Figure 4B:
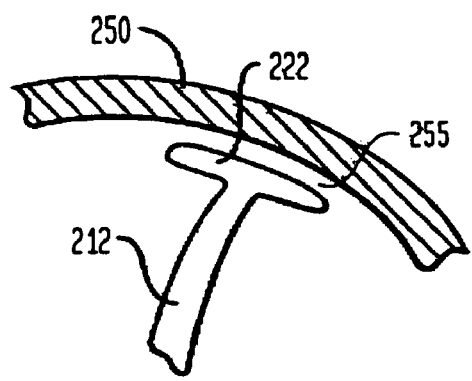
FIG. 4B is a cross-sectional view of the blade of FIG. 4A within a portion of a vessel.

FIGS. 4A and 4B show perspective and cross-sectional views, respectively, of a blade 212 of impeller 200 having a winglet 222 at its distal end. FIG. 4A shows the cross-section of the blade 212 where it joins winglet 222 as a dashed line, the winglet significantly enlarging the cross-section of the blade at its distal end. FIG. 4B shows blade 212 and winglet 222 in cross-section, in which the winglet and blade form an approximate T-shape. As shown in FIG. 4B, the suction side of the blade is on the right, and the pressure side is on the left. If blade 212 has a thickness between the pressure face and the suction face at the distal end of the blade, winglet 222 may have a width between about 1 and 3 times the distal thickness of the blade, measured in a direction parallel to the blade rotation direction. If blade 212 has a chord length, winglet 222 may have a length approximately equal to the chord length.

Winglets 222 are preferably aerodynamically smooth shapes having leading edges where flows impact the edges of the winglets, and trailing edges where flow is discharged from the winglet surfaces. Winglets 222 preferably have smooth aerodynamic cross-sections, generally in the direction of the mean flow, which is parallel to the flow direction along the blade tip surfaces. FIG. 5D shows possible leading edge geometries, including a radius edge 240, a sharp edge 242, and chisel edges 244 and 246.

Where impeller 200 rotates within a conduit 250 for fluid flow, the distal end of blades 212 in the deployed configuration, either with or without a winglet 222, may be located proximate to the interior surface of the conduit, so as to define a tip gap 255 between the blade distal end and the inner surface of the conduit. The tip gap 255 may be about 10 to 50 percent of the maximum thickness of the distal end of the blade. In such circumstances, appropriately shaping the tips of the blades, such as by providing the tips with winglets 222, can improve the quality of the flow field and reduce shear stresses. As shown in FIG. 4B, the winglet 222 may be proximate to the inner surface of conduit 250, a configuration which may be used as a hydraulic bearing for an impeller 200.

For blood pump applications, simulations have shown that most hemolysis occurs at the blade tip, and that winglets lowered the hemolysis. Alternatively, the tip shape may be rounded to reduce hemolysis. A rounded blade tip reduces flow separation and turbulence at the tip compared with a squared-off tip, and winglets further reduce flow separation and hence turbulence in the wake of the blade tip as it moves relative to the fluid. By using a winglet 222, the gap 255 between the tip of blade 212 and the inner surface of conduit 250 may be increased while retaining the performance of an impeller having a smaller tip gap but no winglets. This effect is analogous to retained lift near the end of winglet-equipped airplane wings. Fluid head losses are minimized for a tip gap in the range of about 0.10-0.15 times the maximum thickness of the distal end of the blade for blades without winglets, this range being expected to reduce hemolysis by reducing shear stresses in gap flows. Winglet-equipped blades show minimum fluid head losses at a tip gap of about 0.25-0.30 times the maximum thickness of the distal end of the blade. An increased tip gap reduces shear stresses for impeller operation in a conduit, and for blood pumping applications hemolysis is reduced compared with the use of a smaller tip gap.

Figure 5A:
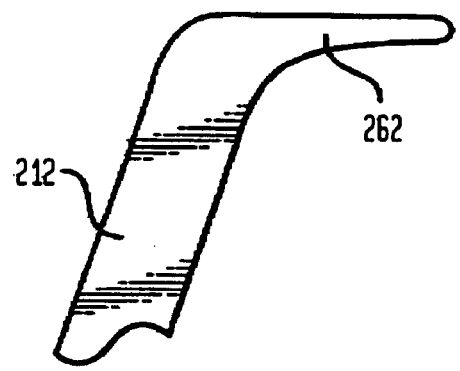
FIGS. 5A-5C are cross-sectional views of blades having exemplary winglet configurations.
Figure 5B:
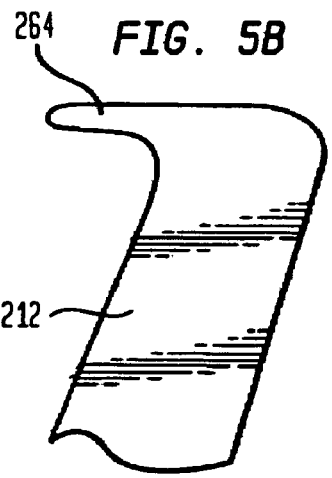

FIG. 5A shows a suction side winglet 262 extending from the outer edge of the suction face of blade 212. This is a view from the leading edge, in cross-section, so that the blade rotates towards the direction of viewing. FIG. 5B shows a pressure side winglet 264 extending from the pressure face of blade 212. The parameters may be similar to the suction side winglet. The function of the pressure side winglet is to reduce flow through the gap 255. There is less effect of creating a hydrodynamic bearing, but the pressure side winglet "scrapes" low momentum fluid off the inner surface of the conduit 250 and prevents this fluid from entering gap 255 and subsequently being used in the core of a tip vortex. This can reduce shearing stresses in the bulk of the fluid flow.

Figure 5C:
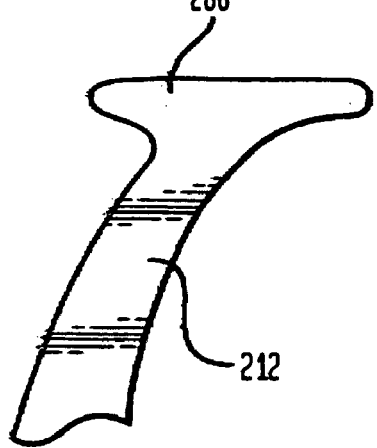
Figure 5D:
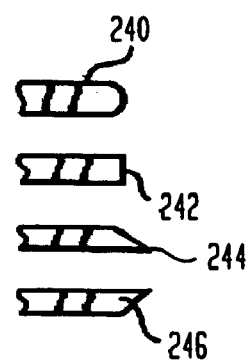
FIG. 5D shows cross-sectional views of exemplary winglet edge geometries.

FIG. 5C illustrates a combined winglet 266 extending from the outer edge of both the pressure and suction faces of blade 212. Embodiments of the present invention include the configurations shown in FIGS. 5A-5C. Numerical methods can be used to design the winglet configurations. Where the blade chord lengths are long and the blade has a significant helical extent, the geometry and shape of the blade tip and the winglet can become complex.

Figure 6B:
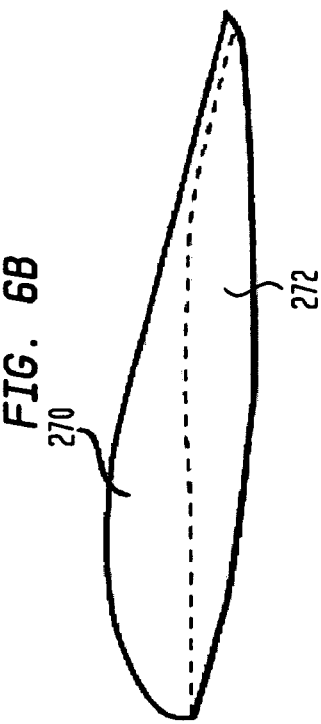
FIGS. 6A-6D are end views of an impeller blade, further illustrating possible winglet configurations.
Figure 6D:
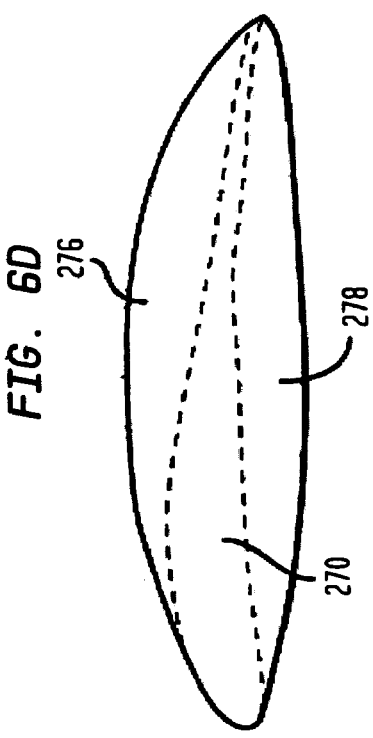
Figure 6A:
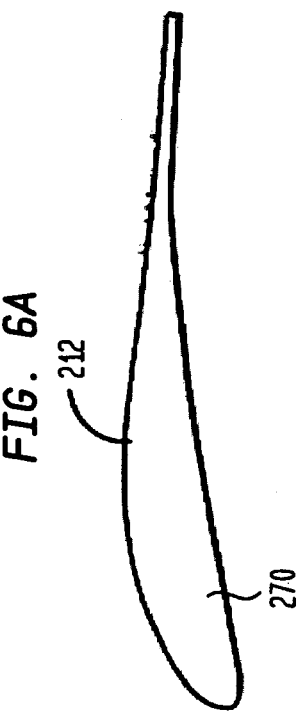
Figure 6C:
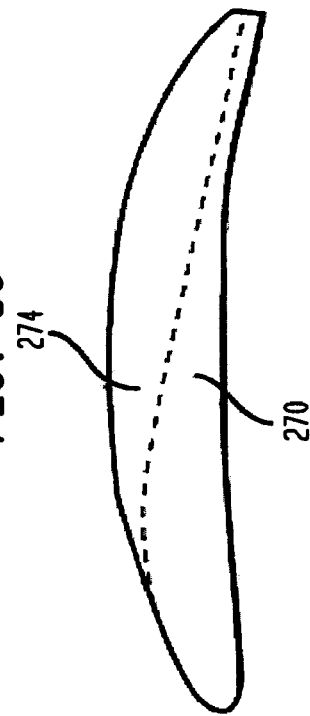

FIGS. 6B-6D further illustrate winglet configurations, the blade supporting the winglet retaining the same shape in these examples. FIG. 6A illustrates the outer edge shape 270 of a blade 212 not having a winglet.

FIG. 6B shows a pressure side winglet extending from the outer edge of the pressure face of blade 212, extending over portion 272. The portion 270 of the winglet corresponds to the original outer edge shape of the blade shown in FIG. 6A.

FIG. 6C shows a suction side winglet, the portion 274 extending from the outer edge of the suction face of the blade, and the portion 270 corresponding to the original outer edge shape of the blade. In some embodiments of the present invention, the pressure side of the blade will have a radius of approximately ⅓ to ½ the blade thickness or width. The extent of the winglet may be from ½ to 3 times the blade thickness. A thickness approximately equal to the blade thickness is shown. The winglet is mostly positioned to the downstream half of the blade as shown. The purpose of this is to create a hydrodynamic bearing in which the outer face of the winglet is in close proximity to the inner surface of the conduit in which the blade is operating. With such configuration, the flow in the gap 255 between the winglet and the inner surface of conduit 250 is reduced in strength, and a tip vortex is less likely to form. This reduces shearing stresses in the fluid. Gap 255 can be between about 10 percent and about 25 percent of the base blade maximum thickness, and is an area that is mostly parallel to the fluid conduit 250. It can be a cylindrical, conical or curved side cylinder where the radius is a function of the axial position of the blade element. Parameters for pressure side winglets and combined winglets (described below) may be similar.

FIG. 6D shows a combined pressure side and suction side winglet extending from both the pressure face and the suction face of the blade, the portion 276 extending from the suction face, the portion 278 extending from the pressure face, and the portion 270 corresponding to the original outer edge shape of the blade.

Features to Aid Stored Configuration

Figure 7A:
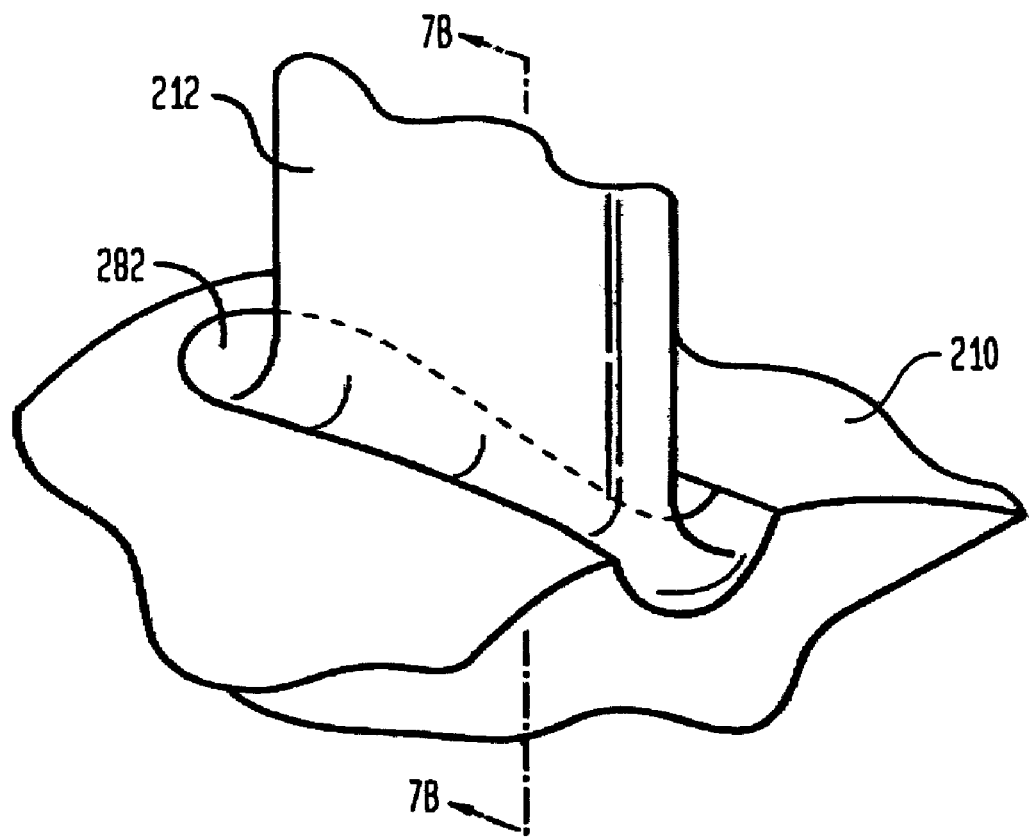
FIG. 7A is an enlarged perspective view of a portion of an impeller according to the present invention having an indentation in the hub surrounding the proximate end of the blade.
Figure 7B:
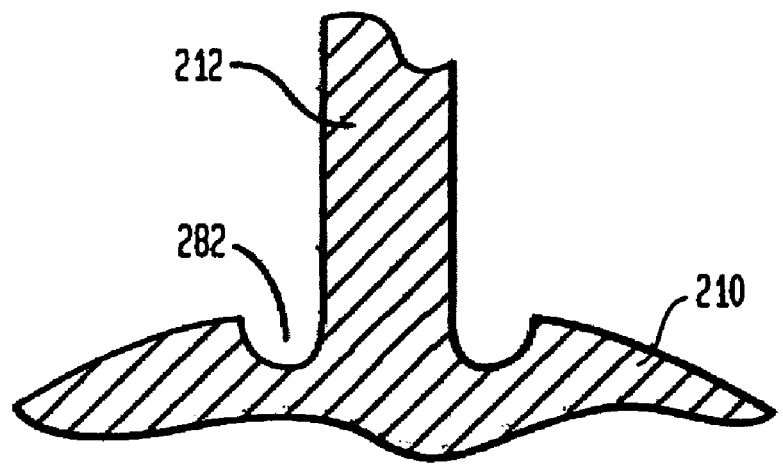
FIG. 7B is a cross-sectional view of the portion of the impeller shown in FIG. 7A.

Referring to FIGS. 7A and 7B, impeller 200 may have one or more structural features which aid achievement of the stored configuration. Such structural features may include one or more indentations proximate to the blade root to facilitate deformation of the blade into the stored configuration. An elongated indentation, such as a trench 282, may be formed in the hub 210 of impeller 200 proximate at least part of the proximal end of the blade (the blade root, where the blade joins the hub). Trench 282 may be formed adjacent to one or both of the suction face and the pressure face of blade 212. Preferably, trench 282 is formed in hub 210 parallel with and adjacent to the proximal end of the blade.

The structural features may facilitate movement of the distal end of blade 212 towards hub 210. For example, a trench 282 around some or all of the blade root can help reduce internal mechanical stresses in blade 212 when the blade is in the stored configuration, for example folded against hub 210.

In some embodiments, blade 212 may have a cross-section in the shape of an airfoil and the indentation may be a curved trench formed in the impeller hub 210 parallel to the proximal end of the blade. Other structural features which may aid achievement of the stored configuration include hinges (such as living hinges) with one or more indentations or cuts, not shown but known in the art, in the blade 212 and/or hub 210; forming a portion of impeller 200 proximate the blade root from a more easily deformable material; and the like.

The indentation may also be referred to as a "dillet," and may include any undermining of the blade root. A dillet may be a trench proximate the blade root, for example having a depth between about 0.5 and about 1.5 times the blade width, and/or a width of a similar size range. A dillet can facilitate folding of the impeller blade towards the hub to achieve the stored configuration.

The dillet may also reduce fluid shear stress and flow vortices in a fluid moving relative to impeller 200 as the impeller operates. In blood pumping applications, lower shear stresses lead to reduced hemolysis of the blood.

Hub 210 may have dillets proximate both faces of blade 212, one dillet facilitating folding of the blade (depending on the direction the blade is folded towards the hub), both dillets reducing the formation of a root junction vortex and hence reducing hemolysis in blood pumping applications. The dillet may be a horseshoe dillet, for example approximating the shape of a horseshoe vortex that would otherwise form at the blade root. Hence, dillets may be provided to reduce shear stresses, even for impeller blades that are not folded.

Blade Materials and Modulus

Impeller 200 may be in the form of a unitary impeller body, including hub 210 and one or more blades 212 formed from a single material. Alternatively, blades 212 and hub 210 may be formed from different materials. Preferably, blades 212 are flexible so that they can be deformed towards hub 210 in the stored configuration. Blades 212 may be formed in any way that allows expansion from a stored configuration to a deployed configuration, the deployed diameter of impeller 200 being larger than its stored diameter.

Blades 212 may be formed from any material that permits the achievement of a stored configuration in which the blades are folded toward hub 210. In that regard, the blades may be formed from a rubbery, elastic or other material having sufficient resilience to expand when the blades are no longer held in the stored configuration, such as when impeller 200 is deployed from a storage housing. The blades may be formed from polymer materials, such as polyurethane or other polymers having suitable elasticity properties. For medical devices such as blood pumps, biocompatible polymers are preferred. The average molecular weight may be chosen within a given range to obtain desired properties. Alternatively, the blades may be formed from other flexible polymers, from expandable foam optionally with a skin, or from other compressible or deformable materials including shape-change or shape-memory materials, and metals. Blades 212 may be formed with both a substantially rigid portion and a flexible portion, the blades being deformed towards hub 210 by deformation of the flexible portion. The flexible portion may include a hinge, such as a living hinge, a narrowed region, a material which is different from the material of the rigid portion, or other configuration.

Blades 212 and (optionally) hub 210 may be constructed of a low modulus polymer, for example a low flexural modulus polyurethane (this term includes polyurethane ureas, which were used to form impellers according to the present invention). Impeller 200 may be a unitary structure, with the blades and hub formed as one from the same material, for example by molding a polymer.

In some examples, blades 212 may have a stiffness approximating that of a thick rubber band. In such embodiments, the blades will have some stiffness, but will deform under operating loads. For example, the material forming impeller 200 may be chosen so as to have a linear modulus at operational stresses, allowing predictable deformation of the blades under load, and a non-linear modulus at the higher stresses used to deform the blades into the stored configuration.

Impeller 200 may have blades 212 formed from a polymer, such as a polyurethane, having a flexural modulus (for operational stresses) between about 3,000 psi and about 30,000 psi, more preferably between about 5,000 psi and about 20,000 psi, and still more preferably between about 7,000 psi and about 10,000 psi. The modulus for operational stresses corresponds to deformations of the impeller during operation, which in some examples may correspond to strains of approximately 5%. The blade thickness may be reduced when using higher modulus materials to achieve the desired flexibility.

Impeller blades 212 may, for example, occupy as much as 95% of the compressed volume of impeller 200 when the impeller is in the stored configuration.

Figure 8:
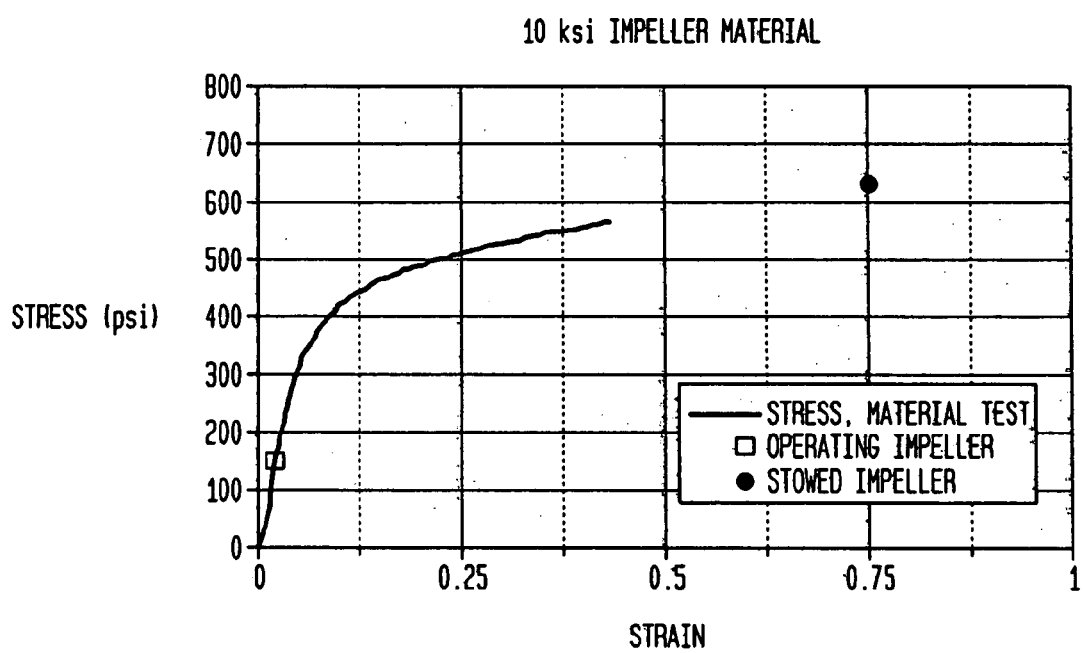
FIG. 8 is a stress-strain graph for a polyurethane material used to form an impeller blade.

FIG. 8 is a stress-strain curve for a non-linear material that can be used to form impeller 200 according to the present invention. The left (low stress) filled circle corresponds to an impeller operating point (stress and strain under operating conditions) and the right (high stress) filled circle corresponds to the impeller stored configuration. The stress/strain relationship is approximately linear at the impeller operating point, so that deformations due to operational stresses can be accurately predicted by numerical modeling. The stored configuration, in which blades 212 are folded against hub 210, is within a high strain non-linear portion of the curve. This allows the stored configuration to be achieved without passing the material tensile failure point, and also reduces the stresses necessary to achieve the stored configuration. In example impellers 200, the maximum material elongation in the stored configuration is about 75 percent.

Preferably, a non-linear material, such as one having the characteristics of FIG. 8, is used for blades 212. This allows the blade material to be relatively stiff at operating loads, and relatively flexible at higher strains, such as when blades 212 are folded in the stored configuration. For example, the strain might be 1-10 percent at operating loads and 75 percent while folded, and the stress/strain curve may correspond to a higher modulus (e.g., 10,000 psi) at operating loads, and to a lower modulus (e.g., 1000 psi) at the higher loads associated with folding. The stress-strain curve may have two approximately linear regions with a sharp change in slope between the operating point strain and the folded strain.

Impellers 200 may be fabricated from commercially available polyurethane polymers, for example having a modulus between about 5,000 psi and about 10,000 psi. Example impellers according to the present invention were fabricated as unitary bodies (including hub and blades) from elastomeric polymers. Example materials used include Conathane™ TU-901 (Cytec Industries, Inc., West Paterson, N.J.), which had a modulus of about 10,000 psi for operational deformations; Conathane™ TU-701 (modulus of about 7,000 psi), and Hapflex™ 560 (Hapco Inc, Hanover, Mass.), which had a modulus of about 5,000 psi. However, other polyurethanes, other polymers or other materials may be used.

A polymer impeller 200 retained in the stored configuration for excessive time periods may not properly deploy, for example due to creep or electrostatic welding between adjacent polymer surfaces. Preferably, impeller 200 is retained in the stored configuration only as long as necessary to insert the impeller to a desired location. Hydrodynamic stress and forward lean may be helpful both to deployment and overcoming any hysteresis effect.

Impeller 200 may deploy from the stored configuration due to stored potential energy associated with blade deformation towards hub 210 in the stored state. However, other stored potential energy may be used (for example, using shape memory materials). Depending on the application, external energy may be conveyed to impeller 200, such as heat (for example, electrical heating of a wire or other structure), centrifugal forces, electromagnetic forces, gas jets, and the like to assist the deployment of the impeller.

Impeller Fabrication

Impeller 200 may be fabricated using precision molding, investment casting (for example, using a hard wax master), stereolithography, milling, or other techniques. Impellers 200 of the present invention have been fabricated using a flexible mold to avoid the presence of significant mold part lines.

Very small impellers, approximately 6-7 mm in diameter in the deployed configuration, may be fabricated from a polymer (such as a polyurethane) and extracted from a precision mold. This allows production of impellers at very low cost. The flexible blades 212 allow the impeller to be extracted from a mold without becoming mold-locked, and allow the use of one-piece molds, instead of multi-part or split molds. This can be advantageous for producing impellers designed for pumping bio-fluids.

Impeller Optimization

Blade shapes can be optimized using standard computational fluid dynamics analysis (CFD). If the impeller material is not flexible, there is no deformation of the impeller when rotating. An improved method of optimizing an impeller 200 formed of a flexible material is to optimize the deployed configuration under operational stress (which may be termed the operational configuration). The impeller can be designed so that the operational configuration is optimized, which is not necessarily the same as the deployed configuration under no loading. A structural computation allows the determination of deformation under the load of operational stresses. Hence, impeller 200 may have flexible blades 212 that deform into an optimized hydrodynamic shape when rotating and operating under design load conditions.

The impeller blade 212 can be designed so as to minimize destruction of delicate particles (such as emulsion droplets, suspensions, biological structures such as cells, and the like) within a fluid. A CFD model may be used to simulate the shear stresses experienced by particles passing through a simulated impeller. Time integrations of intermediate shear stresses experienced by the particles may be used to provide an estimated probability of cell destruction in a biomedical application. A split blade design, in which there are a plurality of blade rows such as discussed above, reduces the residence time in which cells remain in intermediate shear stress regions, allowing an advantageous reduction in cell or other particle destruction compared with a single long helical blade.

The impeller blade(s) 212 may deform during operation, and the optimum configuration of a blade may be achieved only upon deployment and rotation. For example, the optimal design configuration of blade 212 may be achieved only with operational stresses. Hence, blade deformation in operation, due to flexibility of the blade, need not lead to reduced performance. Successful operation can occur even when impeller 200 exhibits significant deflections from a manufactured shape. The impeller can be manufactured with allowance for the deflection included in the design. The configuration of an impeller operating at a predetermined rotation rate, or within a predetermined operating range, can be optimized. Hence, in further embodiments of the present invention, the operational configuration of the impeller, including deformation due to operational stresses, is optimized.

For blood pump applications, CFD optimization may be used to minimize flow velocity over blade surfaces (Reynolds number), vortex formation, flow jets, root junction flows, and to avoid formation of separated flows that may lead to thrombosis.

Reynolds Number

An impeller 200 according to the present invention can operate in a low Reynolds number conduit flow, where the conduit boundary layer comprises a majority of the flow in the conduit. The Reynolds number is the product of blade velocity and chord length, divided by the fluid viscosity. The Reynolds number varies with radius, and generally refers to the tip (distal end) of the blade unless otherwise stated. For example, the Reynolds number for operation of a conventional propeller may be on the order of millions, so that there is a turbulent flow transition as the fluid passes over the blade.

Impellers 200 can be used with flows of small Reynolds number, less than 30,000 for the blade tip, for example the pumping of relatively viscous fluids at low velocity or flow rate. Impellers according to the present invention may operate with blade chord Reynolds numbers of between about 1,000 and about 30,000, preferably between about 2,000 and about 20,000, and more preferably between about 5,000 and about 20,000. The operation at such low Reynolds numbers corresponds to substantially laminar flow of the fluid over the blades. The reduced turbulence leads to reduced shear stress, and reduces hemolysis in blood pumping applications.

Impellers 200 may also be used for flows of larger Reynolds numbers, such as from 100,000 to several million. Impeller diameters can be in the range of several millimeters (or less) to several meters, depending on the application.

For operation in a conduit 250, impeller 200 may be located within a fully developed laminar flow profile, for example at a distance of about 10-15 times the conduit diameter from the conduit inlet.

A plurality of blade rows may be operated at a lower Reynolds number than a single longer serpentine blade having similar hydraulic efficiency. Each blade row may be separately optimized, for example to obtain substantially laminar flow. The blade rows may be clocked relative to one another to reduce hemolysis in blood pumping applications. Flow separations leading to thromboses may be avoided. Further, each blade row may include a different number of blades, for example 1, 2 or 3 blades. Hence, a plurality of blade rows may be used to reduce hemolysis in blood pumping applications compared to a single serpentine blade, while retaining similar or improved efficiency. For example, axial heads may be obtained similar to mixed flow pump heads.

For example, in an impeller 200 operated within a cannula as a blood pump, such as blood pump 600 described below, the blade chord Reynolds number of the first blade row was about 12,600, and was about 15,800 for the second blade row. This suggests that the flow was substantially laminar. In this case, the blades 212 may not exhibit a transition to turbulent flow over the blade surface (where the shear stress suddenly jumps to a higher value), which for blood pump applications leads to lower hemolysis.

Hemolysis

Hemolysis refers to the breakdown or destruction of red blood cells, releasing the hemoglobin contained therein. For blood pumping applications, hemolysis for a given impeller 200 can be estimated using equations known in the literature, and parameters discussed herein adjusted to reduce hemolysis.

Both the hemolysis and platelet activation analyses can be conducted by combining the model of Garon and Farinas, "Fast Three-Dimensional Numerical Hemolysis Approximation," *Artificial Organs*, 28(11):1016-1025 (2004), with empirical correlations of Giersiepen et al., "Estimation of Shear Stress-related Blood Damage in Heart Valve Prostheses—In Vitro Comparison of 25 Aortic Valves," International Journal of *Artificial Organs*, 13 (5), 300-306 (1990). Giersiepen proposed empirical correlations for LDH-release by platelets:

$$\frac{\Delta LDH}{LDH}(\%) = 3.31 x 10^{-6} t_{exp}^{0.77} \tau^{3.075},$$

and for Hb-release by red blood cells:

$$\frac{\Delta Hb}{Hb}(\%) = 3.62 x 10^{-5} t_{exp}^{0.785} \tau^{2.416},$$

where t is in seconds and $\tau$ is in Pascals. The Garon and Farinas model, in short, provides a framework for any damage model of the form $$D = \gamma t_{exp}^{\beta} \tau^{\alpha}$$

by calculating the net flux of the parameter through a volume. So $$D = (D_I)^{\beta}$$
$$D_I = \frac{1}{Q} \int_V \sigma dV$$

and $$\sigma = (\gamma)^{(1/\beta)} \tau^{(\alpha/\beta)}.$$

The variable $\tau$ is the scalar form of the stress tensor referred to as the Von Mises Criterion and is specified as:

$$\tau = \left[ \frac{1}{2} [(\sigma_1 - \sigma_2)^2 + (\sigma_2 - \sigma_3)^2 + (\sigma_3 - \sigma_1)^2] \right]$$

where $\sigma_1$, $\sigma_2$ and $\sigma_3$ are the principal stresses.

According to Garon and Farinas, the normalized index of hemolysis (in g/100 L) is then:

$$NIH = 100 \, HbD,$$

where Hb is the hemoglobin concentration in grams per liter, and the modified index of hemolysis (in parts per million) is:

$$MIH = 10^6 D.$$

By analogy, the platelet activation rate would be given by $$P1A = P1D,$$

where both P1 and P1A are platelet concentrations, for example in thousands per microliter.

Garon and Farinas only considered the hemolysis rate and only in laminar flow, and so the principal stresses are in reference to the laminar viscous stress tensor only. Garon and Farinas made no reference to how turbulent flow would be accommodated, but that discussion does take place in other research. Arvand et al. ["A Validated Computational Fluid Dynamics Model to Estimate Hemolysis in a Rotary Blood Pump," *Artificial Organs*, 29(7):531-540 (2005)] actually advocated neglecting the Reynolds stress term in turbulent flow simulations in order to avoid "numerically caused variety" of the scalar form of the shear stress used in the hemolysis regression model, but the more conventional approach has been to use the effective shear stress (laminar plus Reynolds stress). See, for example, Gu et al., "Evaluation of Computational Models for Hemolysis Estimation," *ASAIO Journal*, p. 202-207 (2005).

Both approaches may be taken and compared for both hemolysis and platelet activation analyses. The flow is simulated using computational fluid dynamics, the shear stress is determined from the determined three-dimensional flow data, and the hemolysis may then be determined from the shear stress distribution.

Stored Configuration and Deployment

Impeller 200 may be stored in a storage housing, such as storage housing 260, transported to a desired location in the stored configuration, and, once at the desired location, deployed into a deployed configuration. Rotation of the impeller then induces fluid flow at the location. For example, the impeller in the stored configuration may have a diameter approximately equal to or less than half the diameter of the impeller in the deployed configuration, the diameter of the stored configuration being generally defined by the inner diameter of the storage housing. The storage housing may be any assembly which acts to hold the impeller in the stored configuration, and may comprise a tube, sleeve, or similar structure inside which the impeller is stored prior to deployment.

In the stored configuration of impeller 200, blades 212 may be folded in towards hub 210, or otherwise deformed or reconfigured so as to present a reduced diameter compared with the deployed configuration. Impeller 200 may be held in the stored configuration by storage housing 260. In the stored configuration, the distal ends of blade 212 are closer to hub 210 than in the deployed configuration, and the stored diameter of the impeller can be significantly less than its deployed diameter. Stored diameters of about one-half of the deployed diameter or less are achievable.

The storage housing need not have a fixed diameter, as does storage housing 260, but may include a non-expandable portion, in which impeller 200 is stored, and an expandable portion, into which the impeller can be moved for deployment. Impeller 200 may then deploy within the expanded portion of the storage housing. The expandable portion of the storage housing may also have a stored configuration. For example, the diameter of the expandable portion in the stored configuration may be approximately half or less of its diameter in the expanded state. Alternatively, the entirety of the storage housing may be expandable such that impeller 200 does not have to be moved axially for deployment.

Storage housings that are expandable or that include expandable portions may be held in a compressed state by a retainer sleeve, described below. Impeller 200 may be stored in a compressed configuration within the storage housing when the storage housing is retained in the compressed state. However, once the retainer sleeve is removed from that portion of the storage housing in which impeller 200 is located, the storage housing and impeller can expand to their expanded or deployed configurations. Impeller 200 may be deployed by urging the impeller blades 212 out of the confines of the storage housing, for example by pulling the retainer sleeve away from that portion of the storage housing overlying the impeller. In some embodiments, the retainer sleeve may be expanded in situ so as to allow impeller 200 to achieve the deployed configuration. Other methods of deploying impeller 200 will be clear to those skilled in the art.

Impeller 200 may be deployed by various methods. For example, the storage housing may be expandable so as to have an expanded configuration when impeller 200 is in the deployed configuration, and a compressed configuration when the impeller is in the stored configuration. In such embodiments, the storage housing acts to radially compress impeller 200 in the stored configuration and allows the impeller to deploy when the storage housing expands. Alternatively, for storage housings that do not expand, impeller 200 may move axially out of the storage housing.

Figure 9:
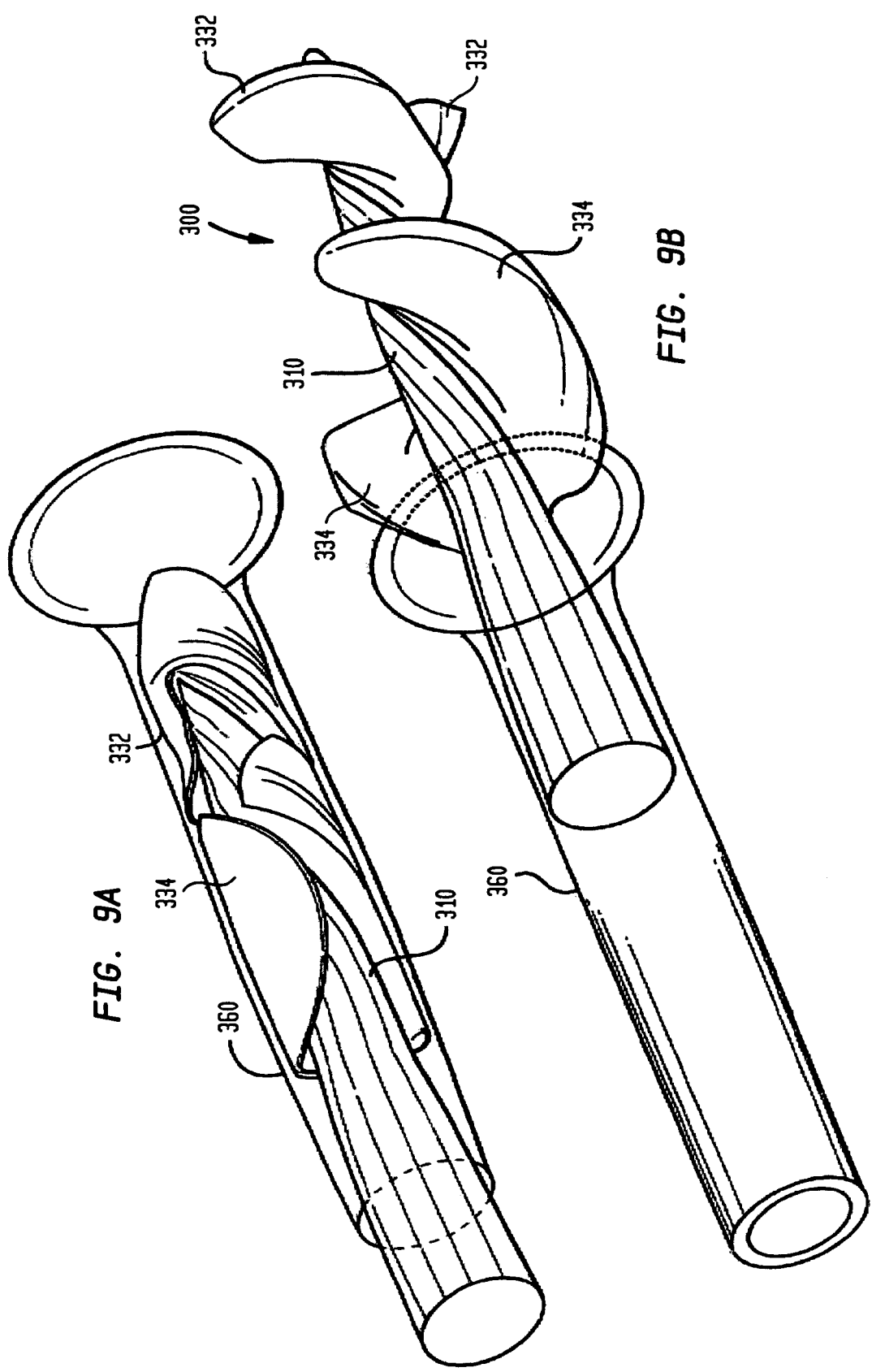
FIG. 9A is a perspective view of an embodiment of an impeller in a stored configuration within a storage housing.
FIG. 9B is a perspective view of the impeller of FIG. 9A after emergence from the storage housing.

FIG. 9A illustrates an impeller 300 in a stored configuration, showing blades 332 and 334 and hub 310. Blades 332 and 334 are kept folded against hub 310 by the storage housing 360. FIG. 9B shows impeller 300 pushed out of storage housing 360 and in the deployed configuration. In the embodiment shown, impeller 300 has two rows of blades, as is seen more clearly in the deployed configuration, the first row including blades 332 and the second row including blades 334.

Figure 10:
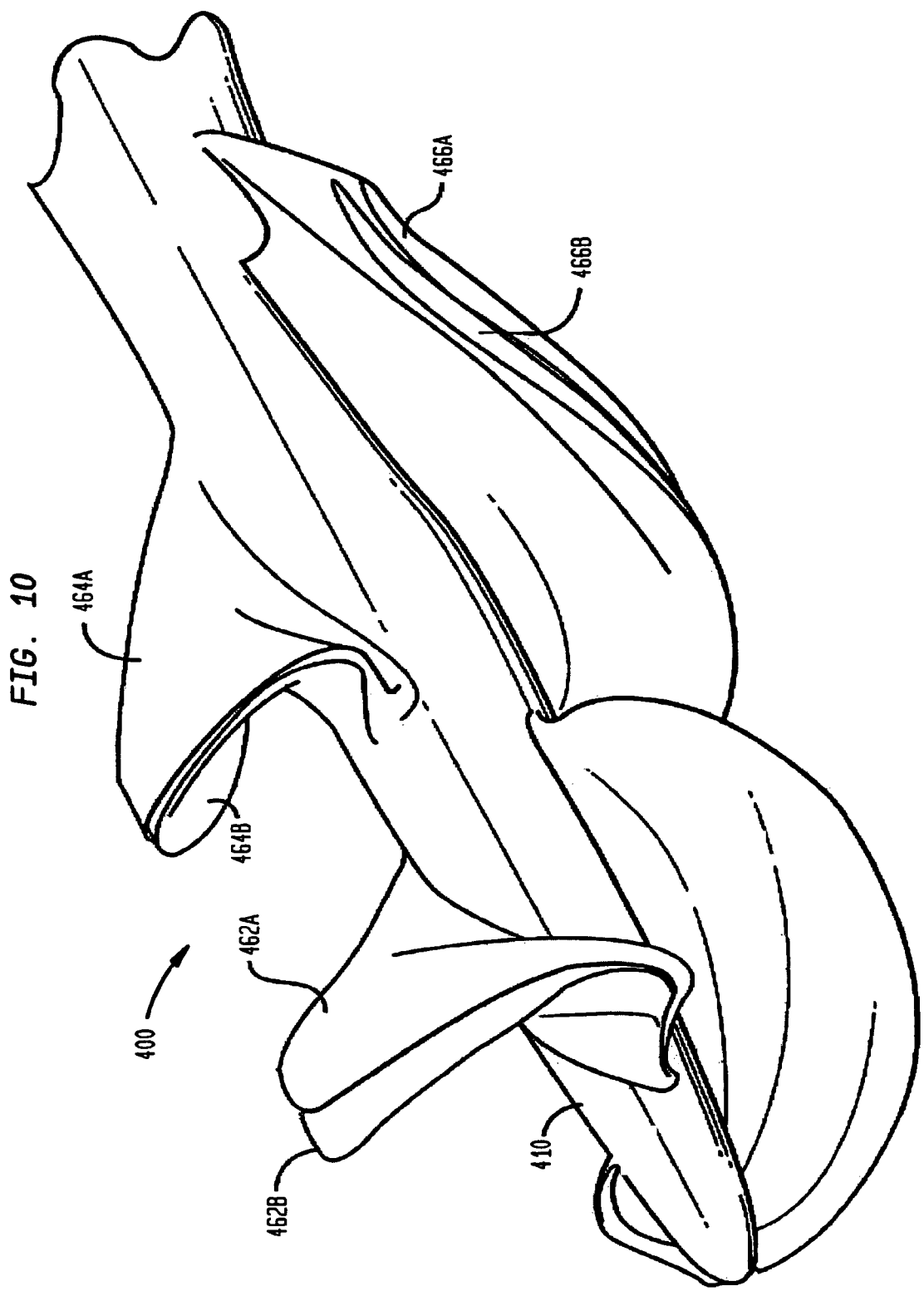
FIG. 10 is a perspective view superimposing deployed and operational configurations of an embodiment of an impeller.

FIG. 10 shows an impeller 400 including a hub 410 and a plurality of blades shown in both the deployed and operating configurations. The figure allows comparison of the deployed configuration under no load with the deployed configuration under operational stresses, when the impeller rotates at the operational rotation speed. In the deployed configuration under no load, the blades assume a first shape indicated by reference numbers 462A, 464A and 466A. When rotating in a fluid, the blades deform to an operational configuration indicated by reference numbers 462B, 464B and 466B. Impeller 400 may be designed so that the flexible blades deform into an optimized hydrodynamic shape when rotating and operating under design load conditions.

In general, the blades deflect forward as the lift on the blades is such that they create thrust, a force directed towards the left side of the figure, moving the blades toward the left side of the picture. The leading edge of the second blade row is obscured. In this example, there are two blade rows, each with two identical blades. For example, the first blade row includes blade 462, shown in an operating configuration at 462B and under a no load condition at 462A. The leading edge of each blade transitions smoothly into the trailing edge at the maximum blade radius. For a hub and blades formed from the same polymer, simulations showed that the hub also deflects slightly in a rotational manner, with the second blade row rotated at the root compared to the first blade row.

Figure 11:
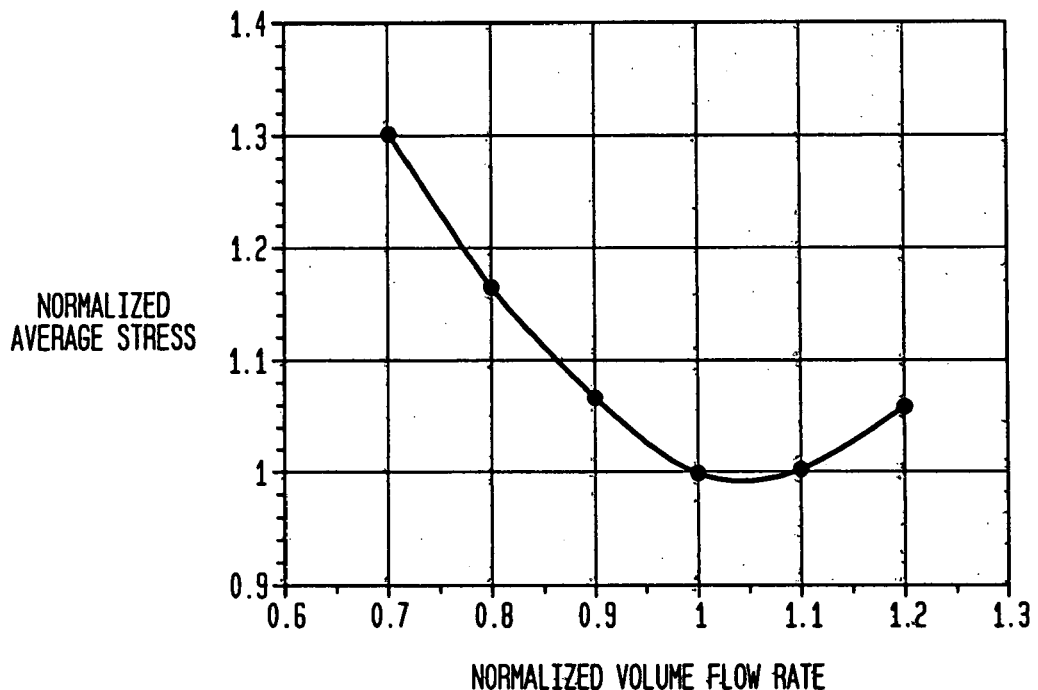
FIG. 11 is a graph showing normalized average fluid shearing stresses as a function of normalized volume flow rates.
Figure 12:
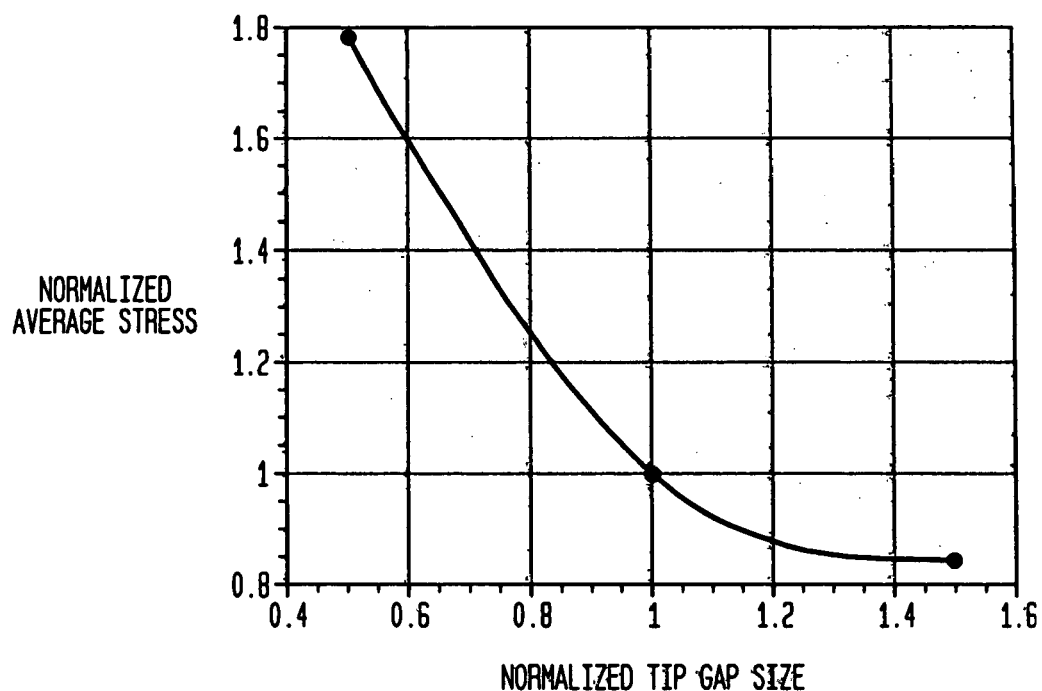
FIG. 12 is a graph showing normalized average fluid shearing stresses as a function of tip gap sizes.

FIGS. 11 and 12 illustrate optimization for fluid shear stress for an example impeller having a design similar to impeller 400 shown in FIG. 10. The distal ends of the impeller blades move proximate to the interior surface of a cylindrical conduit such that the tip gap between the blade distal end and the inner surface of the conduit is about 10 to 50 percent of the maximum thickness of the distal end of the blade.

The curves are double normalized, the design point values both being 1.0, the scales being read as percent of design flow and a factor times the value of stress at the design point. For example, FIG. 11 illustrates that at 70 percent of the design flow, the shear stress is 1.3 times the value at the design condition. FIG. 12 shows that making the tip gap smaller than the design value makes the shear stress higher, whereas making the gap bigger than the design value reduces the shear stress by a smaller factor. Therefore, the fluid shear stress can be reduced to lower hemolysis in blood pumping applications, without significantly compromising pumping efficiency.

Figure 13:
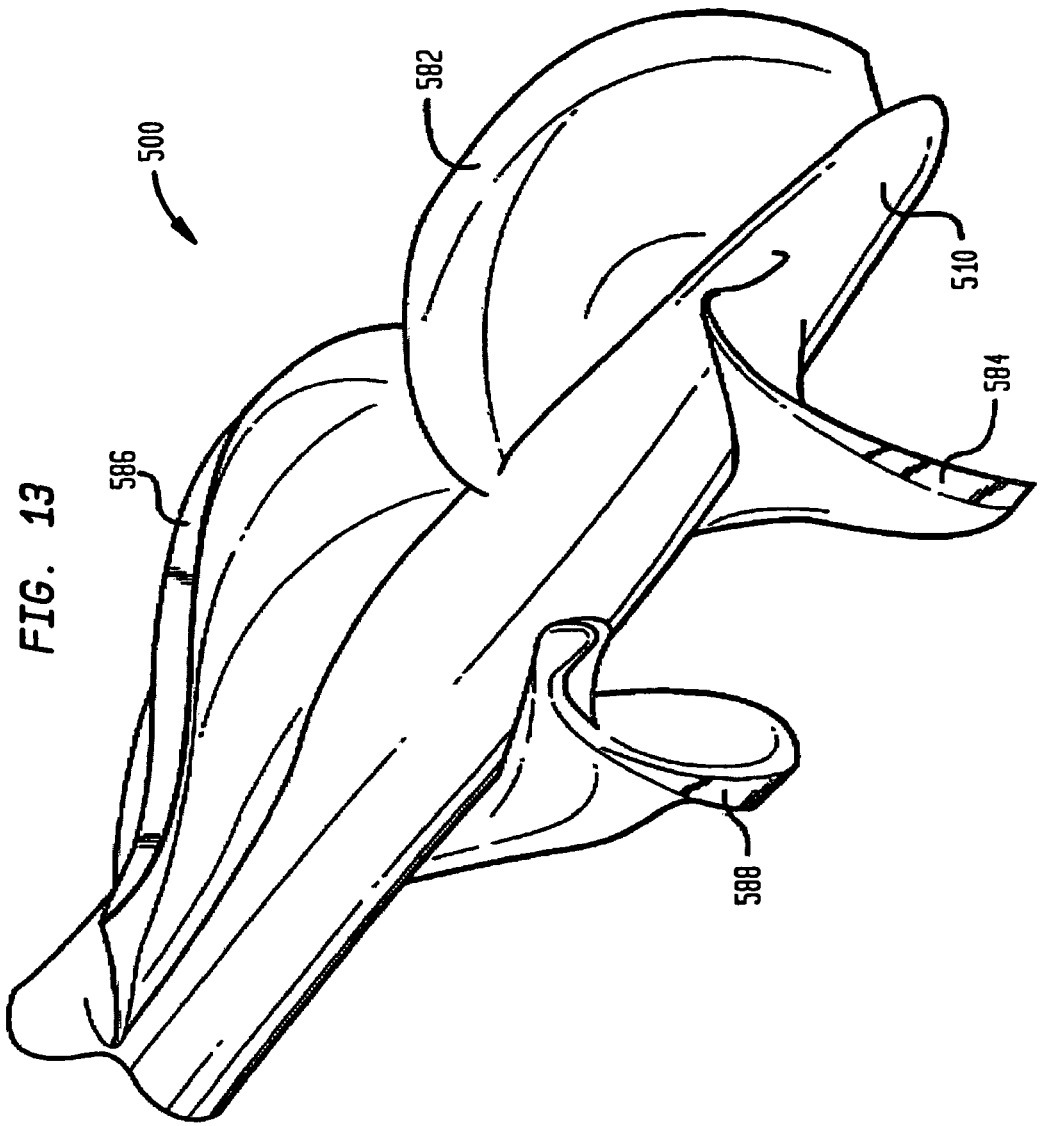
FIG. 13 is a side view of another embodiment of an impeller according to the present invention.

FIG. 13 illustrates an impeller 500 including a hub 510, and two rows of blades having two blades each. The first row includes blades 582 and 584, and the second row includes blades 586 and 588. Impeller 500 has highly curved leading and trailing edge lines where the blade pitch angles are adjusted for local values of relative flow angle. Impeller 500 was designed for operation inside a conduit, such as a cannula having a laminar flow profile, the flow rates being lower near the inside surface of the conduit. This illustration shows the design elements of a low Reynolds number impeller for use in a left ventricular assist device (LVAD) in which the thickness of the boundary layer on the fluid conduit walls approaches the diameter of the conduit. The Reynolds number for a blood pump application was determined to be in the range of 10,000-20,000.

Expandable Impeller and Expandable Cannula

In some embodiments, an expandable impeller is used together with a cannula which may or may not have an expandable portion. If the impeller is not stored in an expandable portion, the impeller must be moved axially for expansion to its deployed configuration. If the impeller is stored in an expandable cannula or in an expandable portion of a cannula, the impeller expands into its deployed configuration with the expansion of the cannula. This combination may be used in improved blood pumps, such as an improved left ventricular assist device (LVAD).

For example, a cannula may be provided that has expandable and non-expandable portions, and the impeller may be stored within, or proximate to, the non-expandable portion. The impeller can be urged out of the non-expandable portion of the cannula into an expanded portion of the cannula. The stored potential energy within the flexible blades of the impeller would then induce self-deployment of the impeller, and the cannula may also self-expand through stored potential energy. The expanded cannula then may have the role of a fluid conduit through which fluid flows when the impeller is rotated. An example of such system is blood pump 600 described below. An expandable cannula and impeller may both be stored within a retainer sheath and deployed together when urged out of the retainer sheath, as is also described below.

Applications

Impellers according to the present invention may be used for a variety of applications, including an axial pump for a fluid (gas or liquid), a motive force for a vehicle, or other applications. Applications of the improved impellers according to embodiments of the present invention include pumps for chemical engineering, propellers for airborne or maritime vessels, water pumps, and the like.

Impellers according to the present invention may be attached to one end of a flexible drive shaft. A torque applied to the other end of the drive shaft is then used to rotate the impeller. The torque may be applied by a rotating member, such as a motor.

Blood Pump

As noted above, impellers according to the present invention are well suited to blood pumping applications, including as a left ventricle assist device, as a right ventricle assist device, for pumping blood to other organs, and the like.

For blood pumping applications, the impeller may operate within the laminar flow profile of a cannula flow, so that the blade pitch preferably varies with radius to match the flow profile. An impeller with two blade rows, such as impeller 500 illustrated in FIG. 13, may have a groove-like feature in the second row blades that takes a helical path from the leading edge to the trailing edge. This arises due to variations in the spanwise loading, and allows an axial flow pump using this impeller to achieve a head rise similar to that of a mixed flow pump.

Computational fluid dynamics analysis shows that an axial blood pump including an expandable impeller with two blade rows was suitable for use in a left ventricular assist device (LVAD). The impeller may be compressed and packaged into a storage housing, such as a tube, cannula, or other structure, for insertion into an object. For an object such as a living subject, the diameter of the storage housing can be about three to four millimeters or less. Having inserted the device, the impeller can be deployed in situ into a geometry that may be about six to seven millimeters in diameter. The impeller then can be rotated using a flexible drive shaft coupled to a drive motor external to the subject. Such impellers may be capable of pumping 4 L/m (liters per minute), and more preferably 5 L/m or greater, for example in a left ventricular assist device (LVAD).

In a representative example of such a device, the impeller may rotate at about 30,000 RPM. The impeller may include two or more airfoil shaped blades that form an axial flow pump, and may be positioned using a guide wire. The guide wire may run within a hollow center of the flexible drive shaft, and the hollow center may also convey saline solution or other fluid for infusion, cooling and/or lubrication purposes. The guide wire may be removed, if desired. Implantation into a living subject may be achieved without surgical intervention through an insertion cannula having a diameter of about 3-4 mm. For example, a device including an impeller and a cannula may be inserted in a stored configuration through an insertion cannula in the femoral artery, the impeller and cannula then deploying (expanding radially) to approximately twice the stored configuration diameter when located at a desired location, such as proximate to the aortic valve.

For medical implantation, a drive shaft comprising a metal braid, a polymer braid or a composite material braid may be used, and the drive shaft diameter may be on the order of 1½ to 2 millimeters, and may be hollow to allow the guide wire to pass therethrough.

An impeller according to the present invention can be operated within a cannula, and a flow of 5 L/m at 100 mm Hg net pressure rise obtained (220 mm Hg across the impeller with pressure losses elsewhere). These parameters are well suited to blood pumping applications, for example within a left ventricular assist device (LVAD).

Figure 14:
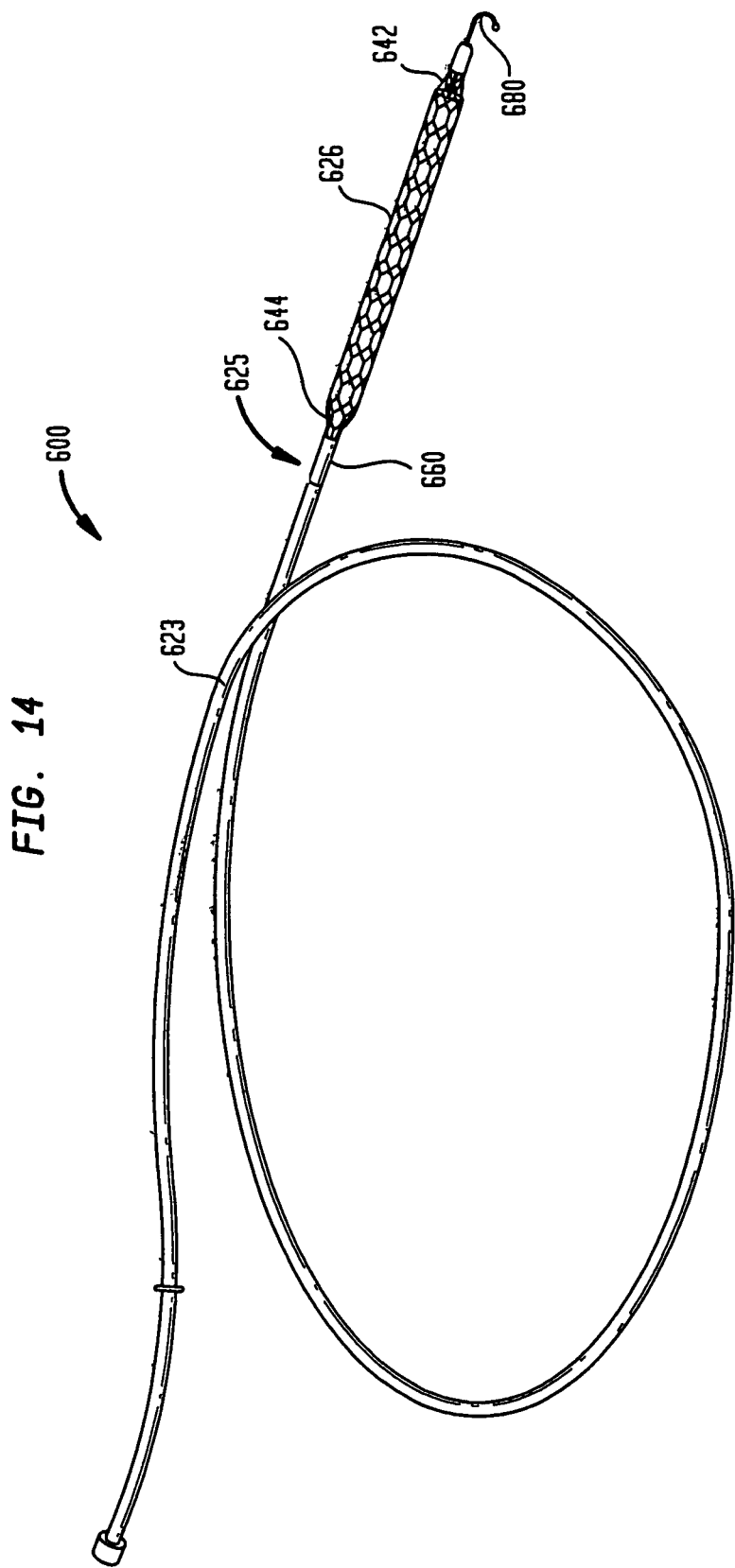
FIG. 14 is a perspective view of a blood pump according to the present invention.

A blood pump 600 for use in blood pumping applications, such as those noted above, is shown in FIG. 14. Blood pump 600 may be broken down into three main parts as shown in FIGS. 15A, 15B and 15C. It should be noted, however, that these features may be combined to produce devices according to the present invention that are intended for applications other than blood pumping applications.

The first part, shown in FIG. 15A, is an impeller 605 with a drive shaft 630 for implementing a rotational drive to the impeller. Impeller 605 includes a hub 610 and a plurality of blades 612, and may have any or all of the features of the impellers described above. Hub 610 and drive shaft 630 may be hollow so as to define in blood pump 600 an internal lumen 670.

The second part, shown in FIG. 15B, is a housing or cannula 625 in which impeller 605 resides. Cannula 625 has a storage housing 660 for impeller 605 when the impeller is in a compressed state. Storage housing 660 may be non-expandable. Alternatively, storage housing 660 may itself be expandable or cannula 625 may have an expandable portion for housing the impeller when the impeller is in its operational or deployed configuration. Whether there is a difference in the location of impeller 605 in its operating and stored configurations depends on whether the impeller is moved axially within cannula 625 for deployment or whether cannula 625 expands in the area in which the impeller is stored.

The third part, shown in FIG. 15C, is a retainer sheath 700 which holds at least a portion of cannula 625 in a compressed state for insertion into a vessel of a patient. Each of these parts will be described more fully below.

The cannula 625 of blood pump 600 has a non-expandable portion 623 at its proximal end and an expandable portion 626 at its distal end. The expandable portion 626 may be flared at one or both ends to aide in fluid flow. The non-expandable portion 623 of cannula 625 may be formed from conventional biocompatible polymer tubing and the like. The expandable portion 626 of cannula 625, on the other hand, may be formed from a mesh 631, such as a metal or polymer mesh, and an elastomer coating 633. The mesh predominantly defines the radial stiffness and bending characteristics of the cannula, while the elastomer coats the mesh to form a continuous duct having a fluid-carrying capability.

Figure 16:
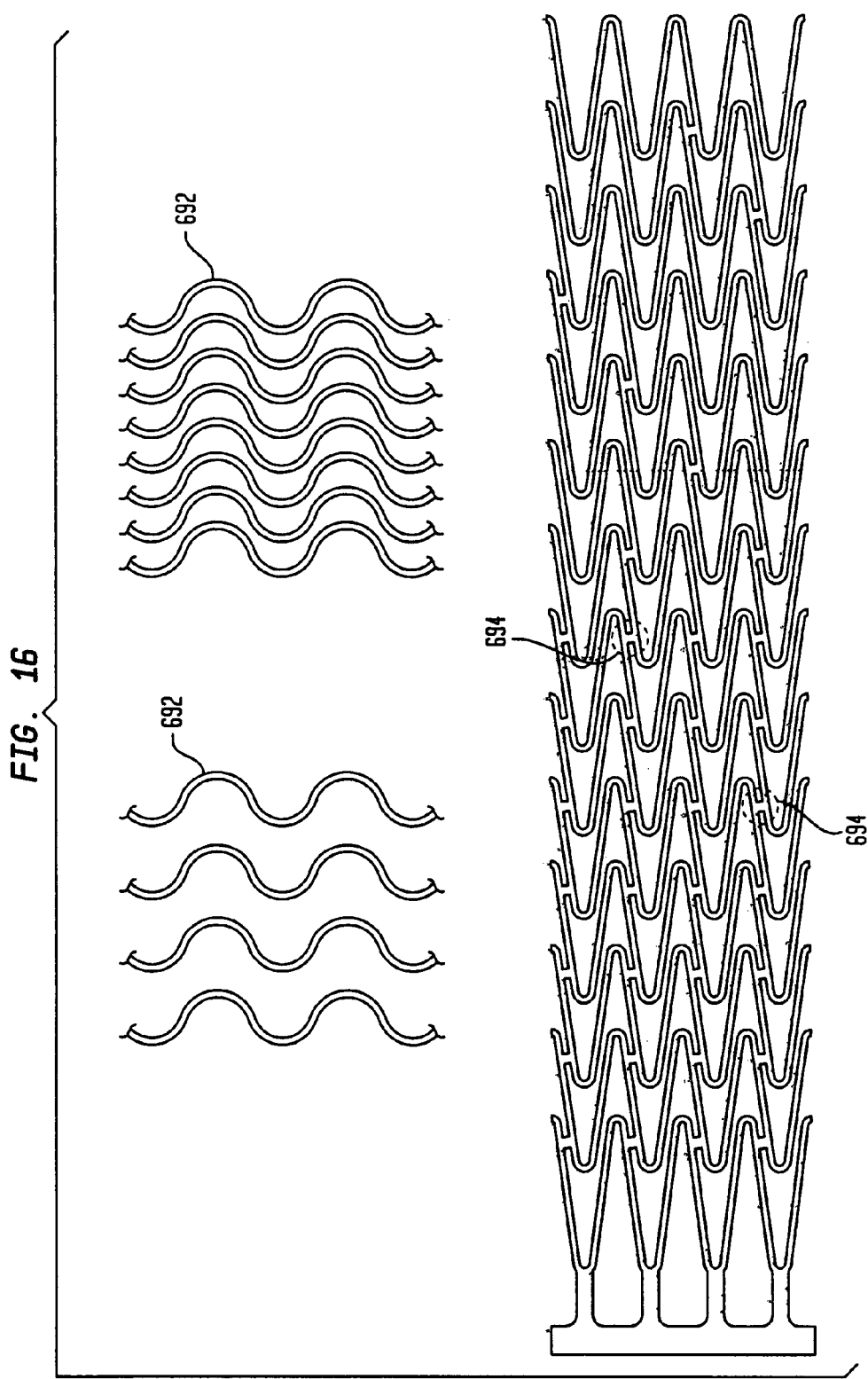
FIG. 16 shows highly schematic side views of different mesh designs.

Mesh 631 may be in the form of a hexagonal cell matrix, or may include circumferential rings 692 and axial connectors 694, as shown in FIG. 16. The circumferential rings predominantly control the radial characteristics while the axial connectors affect axial stiffness and bending performance.

Mesh 631 may be formed from a flexible material, such as a polymer, metal, any shape memory material, or other material, and may include a machined metal cylinder with laser cut voids, a matrix of woven wires, or other configuration. Where mesh 631 is made from a memory metal alloy, such as nitinol, a constant diameter tube of the metal, having a metal thickness on the order of thousandths of an inch, for example, a thickness in the range of 0.005-0.007 inch, may be cut using a laser so as to leave a mesh structure. The constant-diameter mesh may then be expanded/contracted radially to the desired shape using a mandrel, and optionally a clamping mechanism may be used to ensure the mesh conforms to the mandrel geometry. The material is "shape set" to this configuration using, for example, heat treatment. The mandrel, and hence the diameter profile of the expandable portion 626 of cannula 625, optionally can be customized to a particular patient. Alternatively, mesh 631 may be formed from a polymer. Other suitable materials for mesh 631 include other metals (such as alloys, including other memory metal alloys), polymers, other shape memory materials, and the like.

Use of the laser-cutting and shape-setting steps enables complicated geometric patterns to be formed from the constant-diameter tube. An example cannula design may include a bell-mouth inlet (to minimize hydrodynamic losses), a hydrodynamic diffuser at the outlet (for pressure recovery from fluid velocity), a screen-like device at the inlet end (for avoidance of inlet flow obstructions), and additional material at the screen tip that serves as a dilator when the cannula is contracted.

Once mesh 631 has been formed, a coating, such as elastomer coating 633, may be applied to the mesh inner surface, outer surface and/or interstitially. The coating (which may be, for example, biocompatible, corrosion resistant and/or flow improving) may be formed by a solution casting method or by other techniques known in the art, including forming the coating as a separate tube, fitting it over the mesh and heat shrinking it to produce a tight fit. An elastic polymer such as Elastane™ or Biospan™ may be used for coating 633, as may other polyurethanes, or other polymers. Mesh 631 and coating 633 may provide a flexible, expandable portion 626 of cannula 625 that is a conduit for fluid flow. The expandable portion 626 of cannula 625 may be generally cylindrical with a flow inlet 642 at its distal end and a flow outlet 644 at its proximal end.

The mesh 631 is radially expansible in a way which imparts a minimal length change (along the axial direction) during radial expansion/contraction. The expandable portion 626 of cannula 625 may radially contract or expand using stored potential energy, and thus is preferably a self-expanding/self-contracting device.

The radial stiffness of the expandable portion 626 is controllable via the mesh thickness and the geometric density of the cell structure, which can vary along the cannula length. Such variability is useful to match the cannula stiffness with the imposed hydrodynamic loading, enabling a nearly constant radial deflection of the tube when operating as a flow duct (wherein the hydrodynamic pressure varies along the length). This is important in the region of the impeller to provide a constant operational tip gap.

Cannula bending stiffness is also a controllable parameter that may vary axially. For example, where circumferential rings 692 and axial connectors 694 are used to form mesh 631, the bending stiffness is predominantly controlled by the number and placement of the axial connectors, but also depends on the stiffness of the circumferential rings and the stiffness of the elastomer coating 633. The relative placement of the circumferential rings largely affects the radial stability of the cannula during bending. For example, as shown in FIG. 16, mesh 631 may have a substantial amount of interleaving of adjacent circumferential rings. This configuration yields a very stable cannula with respect to radial buckling caused by a bending deflection. Conversely, a mesh pattern with no interleaving yields a cannula that is prone to radial buckling during a bending deflection. Radial stiffness may be augmented via mesh thickness or mesh density. A dense mesh exhibits greater radial stability than a less dense mesh.

Figure 17:
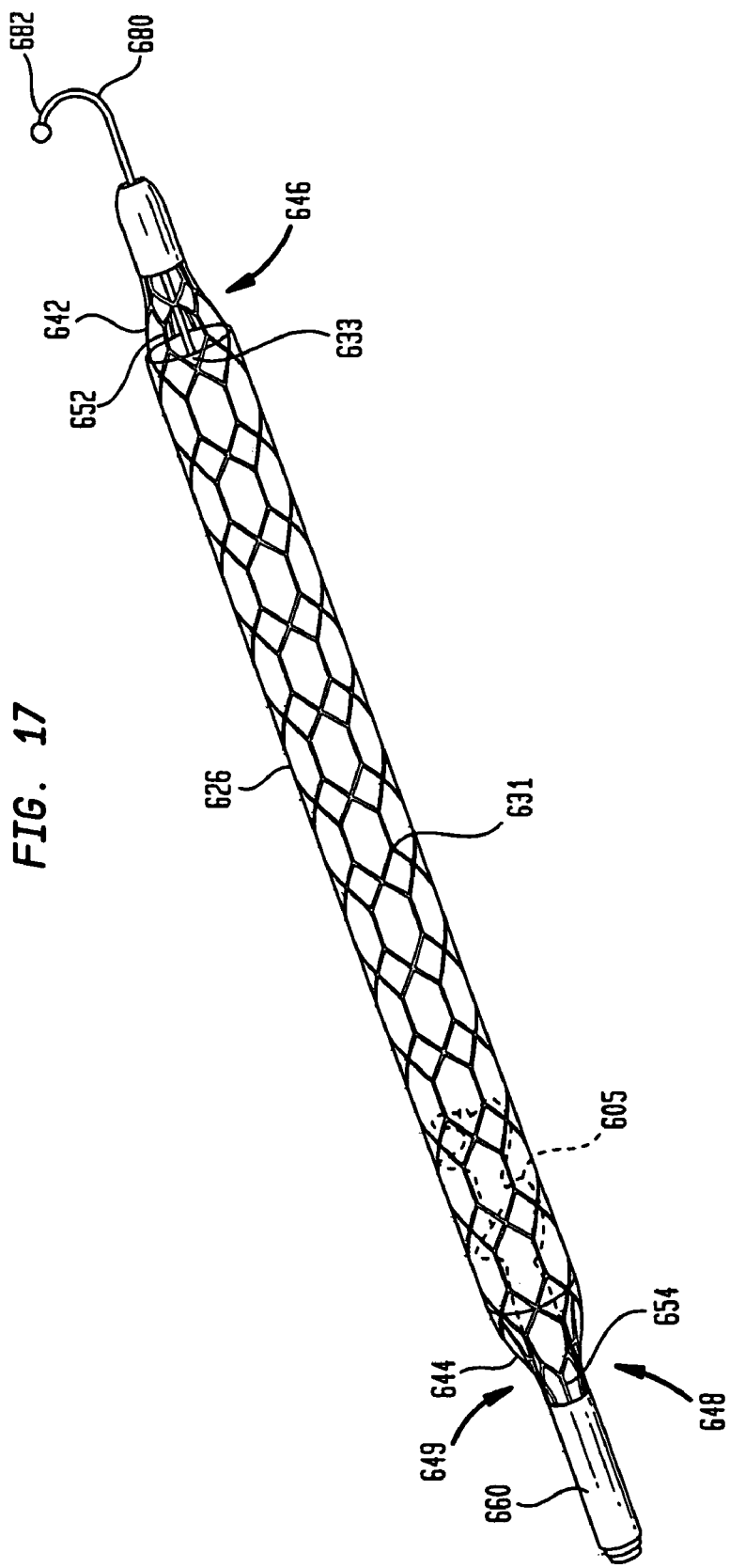
FIG. 17 is a perspective view of the expandable portion of the cannula shown in FIG. 14 in the deployed state.
Figure 18:
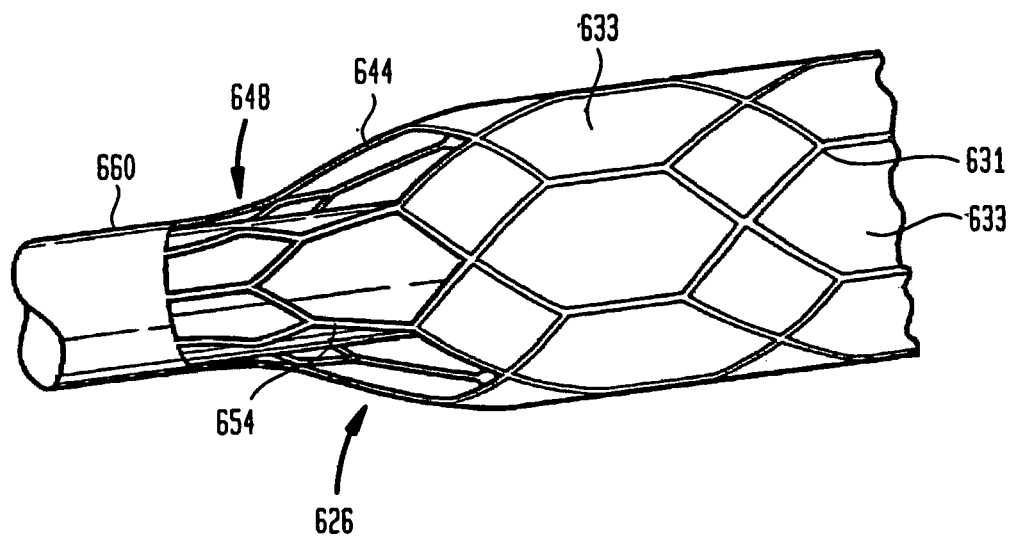
FIG. 18 is an enlarged perspective view of the discharge or proximal end of the expanded cannula having a hexagonal mesh.
Figure 19:
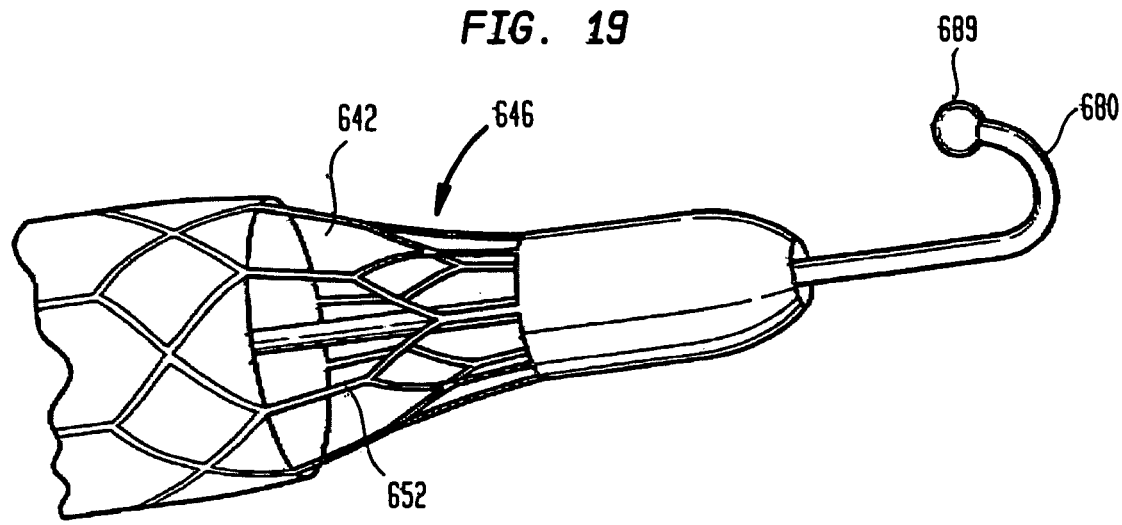
FIG. 19 is an enlarged perspective view of the inlet or distal end of the expanded cannula showing a guide wire having a distal tip.

FIG. 17 depicts cannula 625 in the expanded state. The expanded portion 626 of cannula 625 includes a distal end 646 having an inlet 642 through which blood enters the cannula, and a proximal end 648 having an outlet 644 through which blood leaves the cannula. The portion between inlet 642 and outlet 644 is the expandable portion 626 of cannula 625. Inlet 642 may be provided with a plurality of inlet struts 652 which prevent obstructions from entering the cannula. Similarly, outlet 644 may be provided with a plurality of discharge struts 654 which act as stationary stator blades and remove swirl velocity from the discharge flow of impeller 605. Inlet struts 652 and discharge struts 654 may occupy a short section of the cannula assembly (such as 1 cm) and may be flat linear elements arranged in a uniform circular disposition about the central axis of the device or may be part of mesh 631. Alternatively, struts 654 may be formed with airfoil-type cross-sections. Impeller 605 is located close to the proximal end 648, and a guide wire 680 extends through cannula 625 and through hub 610 of impeller 605. The blood flow through the expanded portion 626 of cannula 625 is from right to left (as shown in FIG. 17) for an LVAD, blood entering the device through the distal end 646 and leaving the device through the proximal end 648.

An uncut region of the original tube retains the original tube diameter and may be used as the storage housing 660 in the form of a cup for retaining impeller 605 in the stored configuration. Storage housing 660 may be referred to as a non-expanded portion of cannula 625 through which blood does not flow. In this case, the expandable portion 626 of cannula 625 is attached to storage housing 660 through the discharge struts 654. Alternatively, the cannula mesh 631, discharge struts 654 and storage housing 660 may be formed from a single tube. The cannula inlet struts 652 can also be formed from the same tube. Hence, the cannula and various attached components can be manufactured from a single piece of tube, for example from a nitinol tube using laser cutting, with a mandrel used for shaping the mesh portion. Alternatively, various portions of the cannula can be manufactured separately and attached together using welding or other attachment techniques. Storage housing 660 may have a flared end 649 which may be defined by the shape of discharge struts 654 to aid in moving impeller 605 back to its stored position.

Impeller 605 may be held in storage housing 660 in the stored configuration and moved axially into expandable portion 626 for deployment, such as by using drive shaft 630 to urge the impeller out of the storage housing. Impeller 605 then unfolds into the deployed configuration using the stored potential energy of blades 612 in the stored configuration. Alternatively, impeller 605 may be held in the stored configuration in the expandable portion 626 while contracted, and may deploy automatically upon expansion of the expandable portion. In still other embodiments, storage housing 660 itself may be expandable, allowing impeller 605 to expand to its deployed diameter without axial movement.

In an example of cannula 625 described above, the expandable portion 626 thereof was formed from a nitinol tube having an inner diameter of 2.62 mm, an outer diameter of 3.02 mm, and a length of 150 mm. In the expanded state, portion 626 had a nominal inner diameter of 6.6 mm in the expanded section, and a nominal length of 133 mm. The expandable portion included 35 circumferential rings 692, four axial connectors 694 per ring in a fully connected region (involving eight circumferential rings), and one axial connector 694 per ring in a minimally connected region (involving twenty-eight circumferential rings). Each circumferential ring 692 had four waves per ring, with a wave amplitude of 5.05 mm (at cut diameter). The interleaved fraction of the rings was 2.05/5=0.41 (where the interleaved fraction for fully interleaved is 1, the interleaved parameter being the overlapped distance divided by the wave amplitude). Finally, the typical thickness of inlet struts 652 and discharge struts 654 was 0.2 mm.

A rotatable drive shaft 630 provides rotational coupling between a motor (not shown), located outside of the patient, and the impeller 605. Drive shaft 630 may have a substantially rigid portion 632 at its distal end which is connected to impeller 605, and a substantially flexible portion 634. The flexible portion 634 of the drive shaft may be housed within a flexible tube 638 which supports the flexible portion and maintains its shape as it is driven rotationally. The proximal end of drive shaft 630 may be connected to the motor for rotating the drive shaft and with it impeller 605. Alternatively, drive shaft 630 may be omitted, and the electric power may be provided through a proximal portion of the assembly to operate a pump motor and impeller 605.

Drive shaft 630 may have a diameter on the order of 1½ to 2 mm, and may be hollow to allow guide wire 680 to pass therethrough. The flexible portion 634 of drive shaft 630 may be formed from a metal or polymer braid which is easily bendable so as to achieve a bend radius on the order of 1 cm. Commercially available flexible impeller drive shafts may be used in blood pump 600, such as those formed from metal wire construction. However, heating problems due to friction between rotating and non-rotating components may occur within any small radius bends required for operation. A composite flexible shaft may be used to reduce such heating problems. The heating problem also can be addressed by providing lubricating or low-friction films on one or both of adjacent surfaces with high relative rotational motion. In that regard, a preferred drive shaft 630 may be constructed from coiled stainless steel, with an optional polymer support tube. A particularly preferred polymer is polytetrafluoroethylene.

The rigid portion 632 of drive shaft 630 may be supported by one or more bearings 672 retained in a bearing housing 675. A saline solution may be directed into bearing housing 675 through internal lumen 670, and the bearing unit end seal 674 may be dimensioned so that a very small quantity of clean saline solution is infused into the patient (approximately 1-2 cc/hr). This fluid flow helps clean impeller 605 and dampens drive shaft vibrations. The fluid flow may also prevent blood from entering bearing housing 675 and compromising its operation and life. If the density of drive shaft 630 is approximately the same as that of the saline solution or other introduced fluid, most of the vibration can be damped. Drive shaft 630 may be formed from carbon or other fiber and polymer composite which has a lower density than metal and more closely matches the density of the saline solution. Other lower density draft shafts and/or higher density fluids may be used for vibration damping. The saline solution or other fluid may be introduced to bearing housing 675 through openings 678 in hollow drive shaft 630.

FIGS. 23A and 23B show an embodiment of blood pump 600 having an axially slidable storage housing 660. As can be seen in these figures, bearing housing 675 may have a reduced diameter portion 677 between its ends housing bearings 672. This reduced diameter portion thus defines a longitudinal space for sliding movement of an internal rib 662 defined by an indented annular channel 664 in storage housing 660. In the deployed condition shown in FIG. 23A, storage housing 660 has been moved proximally by the maximum extent permitted by the engagement of internal rib 662 with a proximal shoulder of bearing housing 675, thereby revealing blades 612 of impeller 605 for deployment. In the stored configuration shown in FIG. 23B, on the other hand, storage housing 660 has been moved distally to the maximum extent permitted by internal rib 662 contacting a distal shoulder of bearing housing 675. In this position, the distal end of storage housing 660 surrounds blades 612 of impeller 605, retaining them in the stored configuration.

The internal lumen 670 of blood pump 600 receives guide wire 680. Together, lumen 670 and guide wire 680 assist in positioning blood pump 600 within the patient. Guide wire 680 may have a two-part structure to assist in threading the guide wire through the bearing/seal assembly and through the hub 610 of impeller 605, since part of that threading may be accomplished under factory controlled conditions, rather than at the time of use. In one embodiment, guide wire 680 may have a J-tip 682 which facilitates navigation of the tortuous arterial pathway from the femoral insertion site to the cardiac left ventricle chamber. Guide wire 680 may include an optional device on its proximal end to allow the attachment of a similar diameter extension of the guide wire, residing in the collapsed cannula 625. The lumen 670 in blood pump 600 may have a relatively large diameter relative to the diameter of guide wire 680. Guide wire 680 may have one or more additional distal end features such as a spherical shape, or a valve plug 689 to plug a hole in impeller 605 after withdrawal of the guide wire (see FIG. 22A).

Optionally, the guide wire channel extending through impeller 605 and the bearing unit end seal 674 may have a valve action, as is known in the art, sealing the guide wire passage after removal of guide wire 680. Guide wire 680 may leave a mechanical seal, not shown, upon removal, or the material of impeller 605 may be designed so as to close the opening into lumen 670 upon removal of the guide wire. This avoids excess saline infusion into the patient.

Blood pump 600 may be inserted into the patient's body using a sheathless insertion procedure. Such procedure may employ a retainer sheath 700 having a distal portion 702 and a proximal portion 704, as shown in FIG. 15C. Distal portion 702 may be about 20 cm in length, and have an inner diameter of about 9 fr (3.0 mm) and an outer diameter of about 10.5 fr (3.5 mm). The inner diameter of the distal portion allows storage of the collapsed cannula/impeller assembly. The proximal portion 704 of retainer sheath may be about 1 meter in length with an outer diameter of about 9 fr. This proximal portion 704 may serve as the housing for the flexible portion 634 of drive shaft 630 and for the non-expandable portion 623 of cannula 625.

Figure 25:
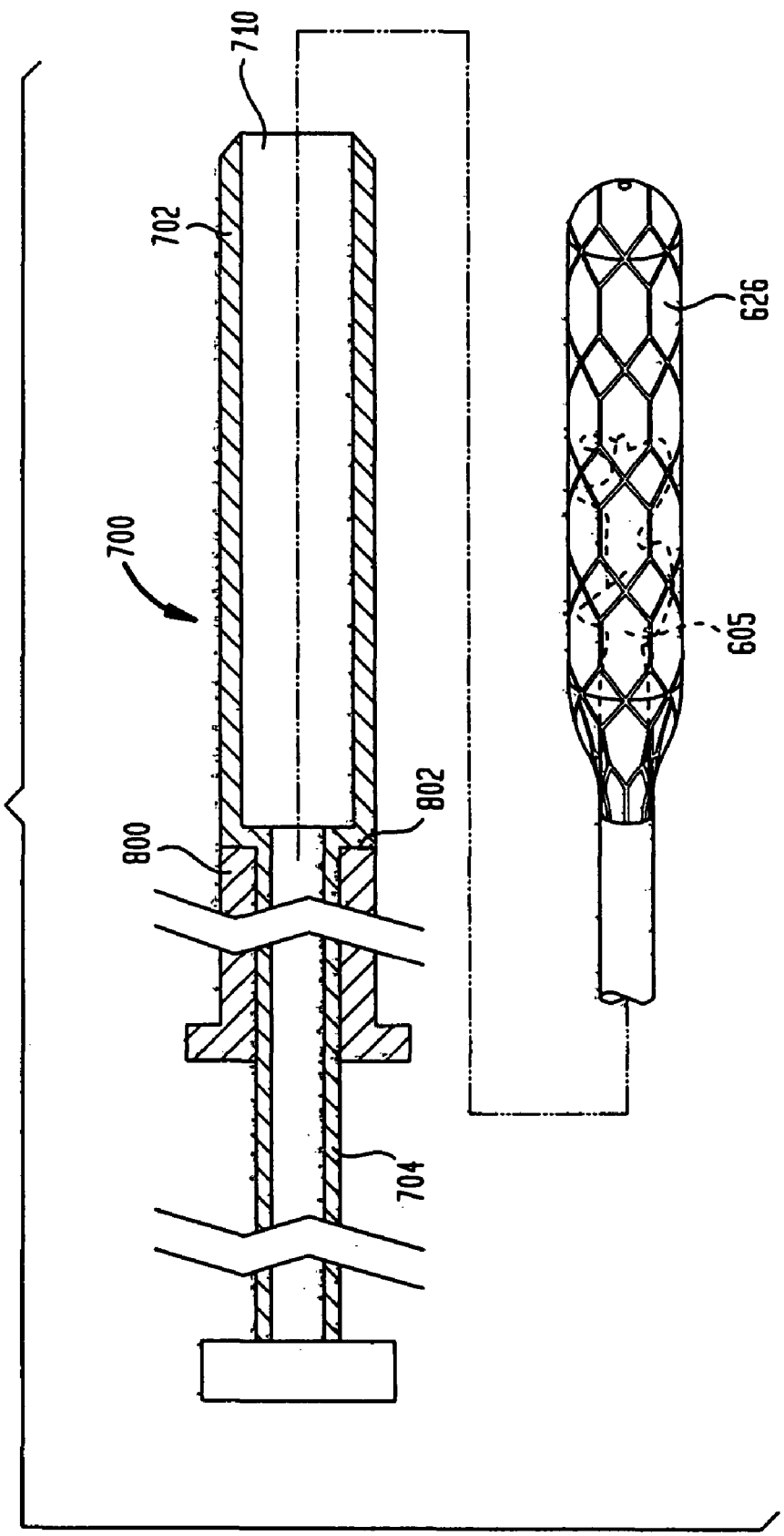
FIG. 25 is a side elevational view in partial cross-section showing a pre-parked sheath embodiment of the present invention.

A "pre-parked" integrated insertion sheath 800 may slide over the proximal portion 704 of retainer sheath 700. The outer diameter of insertion sheath 800 is preferably about the same as the outer diameter of the distal portion 702 of retainer sheath 700, in this example about 10.5 fr. When the proximal end of the distal portion 702 of retainer sheath 700 is pulled up against the distal end 802 of insertion sheath 800, a smooth transition is evident, as shown in FIG. 25. Thus, the combined retainer sheath 700 and insertion sheath 800 may be inserted into the patient's femoral artery as a single entity. After the insertion sheath is fully inserted into the femoral artery, the proximal portion 704 of retainer sheath 700 may be pushed into the patient, pushing the distal end of the retainer sheath and its contents into the patient's left ventricle.

The most distal end 710 of retainer sheath 700 may have a series of slots (not shown) that allow slight expansion of the retainer sheath distal end during removal of cannula 625. As the expandable portion 626 of cannula 625 must be collapsed during this process, the funnel shape created by these slots and the subsequent bending of the material of the sheath facilitates the collapse of the expandable portion of the cannula. Alternate means may be provided to facilitate the recollapse of the expandable portion 626 of cannula 625.

The drive motor rotates drive shaft 630 without rotating cannula 625 or retainer sheath 700. The operation of blood pump 600 is controlled and monitored by a control unit (not shown) which displays status and controls various functions. Sensors, such as a pressure sensor and a flow rate sensor, may be affixed to various regions of the patient and/or blood pump 600.

The control unit preferably displays rpm of the drive motor, patient blood pressures, blood flow rate, information as to the location of the blood pump in the left ventricle, saline infusion and discharge rates, saline infusion temperature, etc. A filter may also be provided to show the presence of debris or blood in the saline discharge stream. The heart rate and blood flow rate are useful to be able to reduce patient dependency on the machine during recovery.

Detailed Description of the Deployment of the Heart Assist Device

Blood pump 600 may be percutaneously inserted through the femoral artery and threaded toward the heart for use, for example, as a left ventricular assist device. Blood pump 600 may be inserted into a patient using conventional cannula insertion methods. The impeller 605 of the device is then expandable in situ to enable an increased blood pumping capacity compared to conventional non-expandable devices. This can eliminate the requirement for surgical intervention.

Insertion may be accomplished using the Seldinger technique which is well known in the art and used daily by surgeons and interventional cardiologists. In such technique, an introducer needle (not shown) is inserted into the femoral artery and used to introduce guide wire 680. Once guide wire 680 is in place, the needle is withdrawn. An optional predilator (not shown) can be used over guide wire 680 to open up the arteriotomy (an opening in the femoral artery) to a size appropriate for insertion of blood pump 600.

Figure 20:
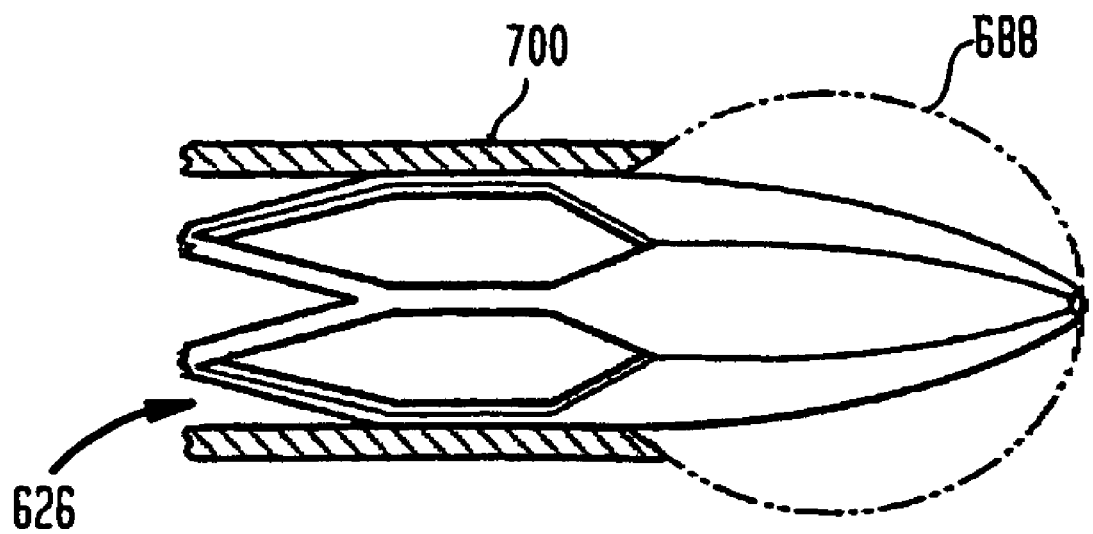
FIG. 20 is an enlarged longitudinal cross-sectional view of an alternate embodiment of the distal end of the cannula forming a dilator.

A guide wire extension 685 (see FIG. 26) contained within the collapsed cannula 625 may be attached to the attachment device at the proximal end of guide wire 680. By fixing the guide wire extension at the proximal end of guide wire 680, the entire assembly is moved along the guide wire through the femoral artery opening previously created. During this process, the attachment of guide wire 680 to the guide wire extension 685 enters the body of the collapsed cannula assembly. To facilitate insertion without an introducer sheath, the distal end of the device may be provided with a tapered distal end dilator 688, shown in FIGS. 20 and 22. This may be a compressed form of the inlet 642 of cannula 626 in which the inlet struts 652 fold down into a tapered, closed configuration similar in profile to a conventional dilator tip.

The blood pump 600, in its collapsed state, is then threaded over guide wire 680 and inserted into the artery. Once blood pump 600 is positioned, guide wire 680 may be removed. A nose bearing or seal at the distal end of impeller 605 can then seal the guide wire opening through the hub 610 of the impeller. This allows saline solution to be injected into impeller 605 for cooling and lubrication purposes, as well as to prevent blood from entering the lumen 670 of blood pump 600.

At the time of insertion, the expandable portion 626 of cannula 625 and impeller 605 are collapsed and may be contained within retainer sheath 700. As described above, the proximal end 704 of retainer sheath 700 may include an optional second integrated insertion sheath 800 which replaces the function of the separate introducer sheath when the device is positioned in place. If there is no "introducer" sheath present during the insertion of the assist device into the femoral artery, the process is referred to as sheathless insertion. In FIG. 25, a smooth transition from the diameter of insertion sheath 800 to the maximum diameter of retainer sheath 700 is shown.

During the insertion of blood pump 600, the transition region has effectively zero length and zero change in outer diameter. The transition region is the region where the enlarged distal portion 702 of retainer sheath 700 meets the end 802 of insertion sheath 800. After the collapsed cannula assembly is inserted into the femoral artery, and the position of insertion sheath 800 is fixed at the patient boundary, the transition region will be located several centimeters past the femoral artery opening. At this point, the medical practitioner holds the exterior of insertion sheath 800 stationary and continues to push the retainer sheath assembly along guide wire 680, until the distal end of the collapsed cannula and retainer sheath reside at the distal end of the guide wire, within the left ventricle cavity 900.

Figure 26:
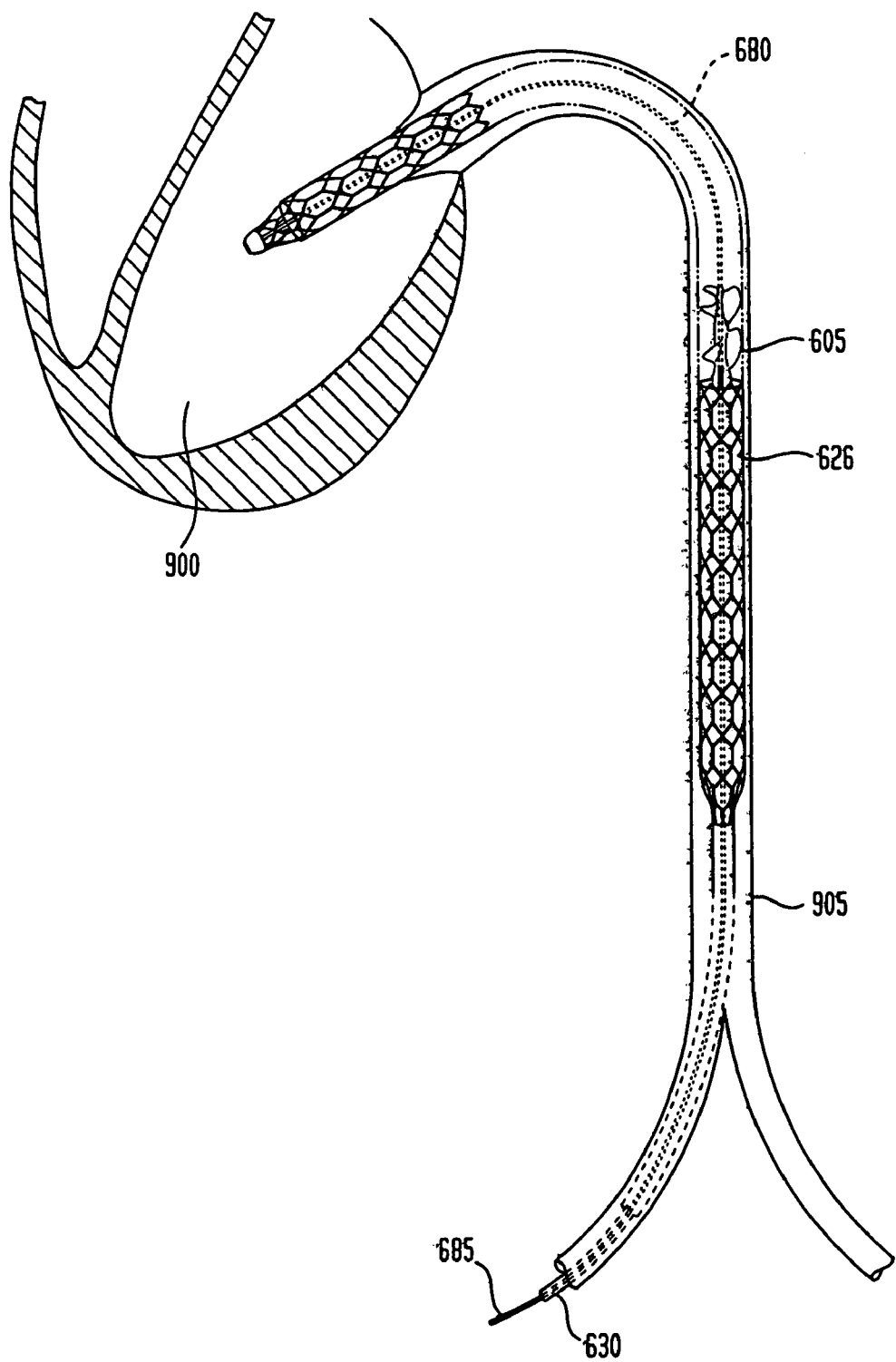
FIG. 26 is a highly schematic view showing the blood pump deployment in a patient.

A possible location of the device for LVAD use is shown in FIG. 26. The non-expandable portion 623 of cannula 625 extends from the descending aorta 905 and into the femoral artery, from which it exits the host body. Guide wire 680 may be advanced into the left ventricle 900 using an optional guiding catheter (not shown), and a fluoroscope may be used to establish proper positioning of the assist device.

Once blood pump 600 is properly positioned, retainer sheath 700 may be retracted, by a dimension of about 15 cm for some embodiments, allowing the expandable portion 626 of cannula 625 to expand to the deployed configuration.

The final step in deploying blood pump 600 involves pushing impeller 605 from its stored position within storage housing 660 and positioning it at a specified location within the expanded portion 626 of cannula 625. This may be accomplished by applying a small force to drive shaft 630 while holding retainer sheath 700 at a fixed location. Retainer sheath 700, in turn, holds the expanded portion 626 of cannula 625 at a previously fixed location. Once no longer restrained by storage housing 660, impeller 605 expands to the deployed configuration due to the action of stored strain energy.

The expandable portion 626 of cannula 625 may attain its deployed configuration through the action of stored strain energy (potential energy). This process reveals the cannula inlet 642, the expanded portion 626 of the cannula and the cannula outlet 644. Successful operation requires that the cannula inlet 642 reside in the left ventricle 900 of the heart and that the outlet 644 reside in the aorta. A fluid seal must exist where the cannula is proximate to the aortic valve, and the surface smoothness of the cannula is preferably such that clinically significant abrasion of the aortic valve is prevented. Also, distal end struts 652 form an inlet grid which prevents the inlet from becoming blocked by soft tissues within the left ventricle.

Impeller 605 may be moved toward the distal end of cannula 625 which curves around through a valve into the left ventricle 900 of the heart, while the flexible portion 634 of drive shaft 630, coupled to impeller 605, extends outside of the body of the patient and is rotated by a drive motor. The non-expanded portion 623 of cannula 625 similarly extends through the femoral artery and outside of the patient. The inlet 642 and struts 652 at the distal end of cannula portion 626 allow substantially unrestricted flow of blood into the device, where it is driven by impeller 605 outside of the device through a discharge mesh or struts 654 at the proximal end 648 of cannula portion 626.

Other methods of expanding impeller 605 may be used. One possible alternative approach may include infusing a liquid or gas through a shaft to inflate impeller 605. Another approach may use rotational forces to induce blades 612 to form a desired shape. The potential energy in the blades, particularly in the blade roots, may be used to deploy the blades into their unstrained position, and hydrodynamic forces may cause the blades to further deform into their operating configuration.

The retainer sheath 700, previously retracted, serves to fix the position of the entire assembly within the patient. Blood pump 600 is now deployed and ready for connection to supporting equipment and use.

When the patient recovers and can be weaned from the necessity of using blood pump intervention, impeller 605 may be pulled back into an inactive compressed configuration in storage housing 660 or in a non-expandable portion 623 of cannula 625, and the expandable portion 626 of the cannula may be pulled into retainer sheath 700. Slots (not shown) or an outward flare 649 (see FIG. 9) may be provided at the distal end of storage housing 660 to assist in retraction of cannula 625. Retainer sheath 700 may then be pulled into proximity with insertion sheath 800, and the insertion sheath, retainer sheath and cannula within it may be removed from the patient through the original femoral artery site. Subsequently, the wound in the patient may be closed in a conventional fashion. The flow rate and pressure rise of blood pumped by blood pump 600 is greater than current non-collapsible devices of the same diameter, and the rate of blood damage (hemolysis) is maintained at a clinically acceptable low level. The use of the device as an RVAD is similar to that described above.

The expansion feature of blood pump 600 is an advantage over non-expandable prior art devices. If the device were non-expandable, the maximum cross-section would be limited to approximately 3 mm to allow for percutaneous insertion. However, this cross-section is insufficient to achieve sufficient blood flow to maintain the health of the patient.

Other applications of the device according to the present invention include providing additional blood flow to other organs, assisting the heart during operations, and the like.

Figure 21A:
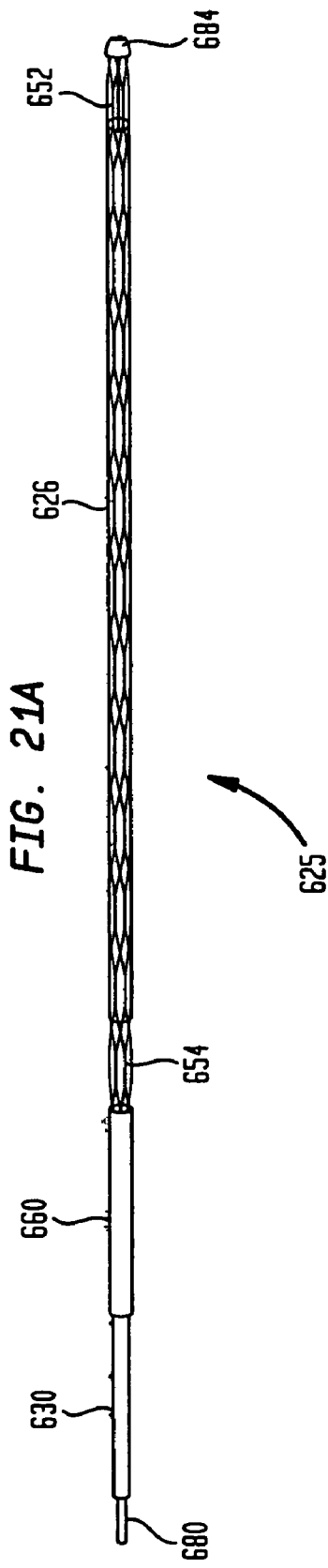
FIGS. 21A and 21B are side elevational views of the expandable portion of the cannula in stored and deployed configurations, respectively.
Figure 21B:
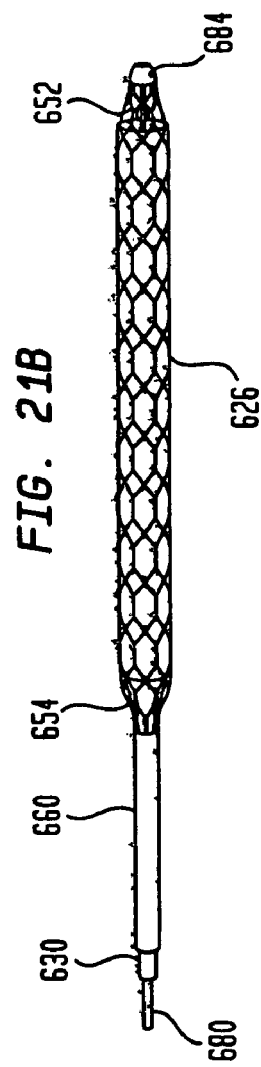
Figure 24:
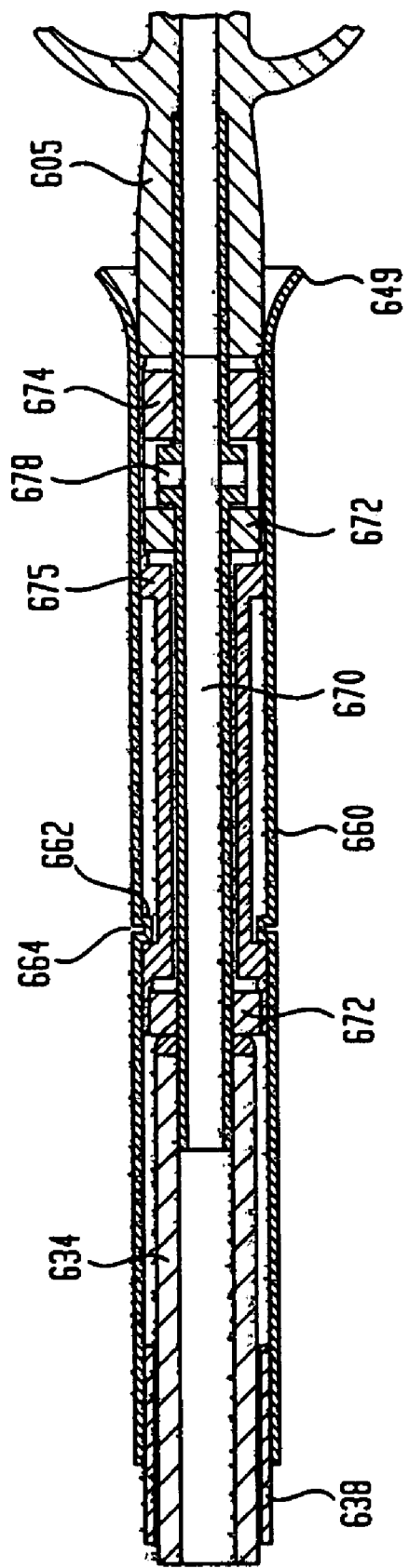
FIG. 24 is a longitudinal cross-sectional view of an alternate embodiment of a blood pump in its deployed configuration.

The expandable portion 626 of cannula 625 may be expanded by any desired method. In one approach, mesh 631 may expand in a radial direction when the expandable portion 626 is contracted along an axial direction, for example using a mesh 631 having a hexagonal structure. In this approach, by applying tension to guide wire 680 through bullnose grommet 684, shown in FIG. 21A, the expandable portion 626 of cannula 625 can be shortened in the axial direction, providing radial expansion into the expanded state. Where a shape-memory material is used for the expandable portion of the cannula, the cannula will achieve its expanded state as the shape memory material reaches a predetermined temperature, such as when the cannula is inserted into a patient's blood vessel. Both impeller 605 and cannula 625 in their stored configurations may be held within retainer sheath 700, whereby both may be mechanically deployed or may self-deploy when removed from the retainer sheath.

Cannula 625 may have at least two configurations, including a stored configuration and an expanded (deployed) configuration. When used as part of a blood pump, cannula 625 in the deployed configuration may be about 20-30 cm long with a diameter of about 6-7 mm. In the stored configuration, cannula 625 may have a diameter of about 3 mm, allowing non-surgical insertion of blood pump 600 into a human subject through a femoral artery. The larger deployed diameter allows for higher fluid flow rates after insertion, and reduced friction pressure losses compared with a non-surgically inserted blood pump having a non-expandable cannula.

An improved process for blood pumping within a living subject includes providing an expandable impeller, inserting the impeller into a patient in a stored configuration (for example, with a diameter of between about 3 mm and about 4 mm), positioning the impeller at a desired location within a blood vessel of the patient, deploying the impeller (for example, to a diameter of between about 6 mm and about 7 mm), and operating the impeller in an operating configuration at a Reynolds number of between about 1,000 and about 30,000, and preferably between about 2,000 and about 10,000. Higher Reynolds number operation and more efficient pump operation may be possible with higher rotation speeds, but may increase the destruction of structures within the pumped fluid, such as blood cells. The operating diameter of the impeller may be at least about 50% greater than the stored diameter. In other examples, the operating diameter may be at least about 100% greater than the stored diameter. For animals, components may be scaled according to the size of the animal.

Novel configurations and material choice allow the improved device to be compressed for cannula insertion into a patient. Representative devices include an expandable impeller, and a cannula that is at least in part expandable, inside of which the impeller rotates. Both the expandable impeller and the cannula have stored states that allow cannula insertion into a vein or artery using non-surgical methods. After insertion and location of the device, the expandable impeller and cannula expand into deployed states. The impeller can be driven through a flexible drive shaft from a drive motor external to the host, or using a motor proximate to the impeller, possibly integrated with a bearing system.

Other Pump Applications

Applications of the improved fluid pump designs described herein are not limited to ventricular assist devices. The improved cannula and impeller designs are useful for any application where a stored configuration having reduced diameter is useful for locating the pump at a desired location. For example, a fluid pump operating underground may be introduced into a pipe, channel, or cavity through an opening of lesser diameter, and operate at a diameter greater than that of the opening used. Applications of an impeller deploying within an expandable cannula include a collapsible fire hose with an integral booster pump, a collapsible propeller, a biomedical pump for a biological fluid, and the like.

In other examples, impellers may also be formed from metal sheets, plastic and non-resilient materials, for example in foldable configurations. Deployment may include the use of motors or other mechanical devices to unfold blades, automatic deployment induced by centrifugal forces, and the like.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An apparatus for inducing motion of a fluid relative to the apparatus, the apparatus comprising:
   an elongated cannula having a proximal portion and a distal portion, the proximal portion including a conduit having a fixed diameter, and the distal portion including an expandable cannula having a diameter expandable to a diameter greater than the fixed diameter; and
   an impeller positioned in the elongated cannula and having a deployed configuration and a stored configuration, the impeller including
   a hub; and
   a plurality of blades supported by the hub, each blade having a proximal end attached to the hub and a distal end, wherein at least one of the proximal and distal ends of a first blade is at least partially offset along the longitudinal length of the hub from at least one of the proximal and distal ends of a second blade, the blades in the deployed configuration of the impeller extending away from the hub, and the blades in the stored configuration of the impeller being compressed so as to move the distal end of the blade towards the hub.

2. The apparatus as claimed in claim 1, wherein the impeller is positioned in the expandable cannula.

3. The apparatus as claimed in claim 1, further comprising a retainer sheath having an inner lumen, the elongated cannula being mounted in the inner lumen for sliding movement relative to the retainer sheath.

4. The apparatus as claimed in claim 3, further comprising an insertion sheath adapted for axial sliding movement over the retainer sheath.

5. The apparatus as claimed in claim 4, wherein the retainer sheath has at least a first stop point, and the insertion sheath is constrained in its sliding movement by at least the first stop point.

6. The apparatus as claimed in claim 4, wherein the retainer sheath has an outermost diameter and the insertion sheath has an outer diameter substantially equal to the outermost diameter of the retainer sheath.

7. The apparatus as claimed in claim 3, wherein axial movement of the elongated cannula relative to the retainer sheath in one direction results in expansion of the expandable cannula and axial movement of the elongated cannula relative to the retainer sheath in a direction opposite the one direction results in compression of the expandable cannula.

8. The apparatus as claimed in claim 3, wherein the elongated cannula is movable relative to the retainer sheath between a first position and a second position, the expandable cannula in the first position being held at the fixed diameter, and the expandable cannula in the second position being expanded to a diameter greater than the fixed diameter.

9. The apparatus as claimed in claim 1, further comprising a drive system operable to rotate the impeller.

10. The apparatus as claimed in claim 9, wherein the drive system includes a drive shaft, and axial movement of the drive shaft relative to the elongated cannula causes axial movement of the impeller relative to the elongated cannula.

11. The apparatus as claimed in claim 10, wherein axial movement of the impeller relative to the elongated cannula in one direction places the impeller in the deployed configuration and axial movement of the impeller relative to the elongated cannula in a direction opposite the one direction places the impeller in the stored configuration.

12. The apparatus as claimed in claim 10, further comprising a bearing system for supporting the drive shaft for both axial and rotational movement of the impeller.

13. The apparatus as claimed in claim 1, wherein the expandable cannula is formed from a tube of flexible material supported by a reinforcing matrix.

14. The apparatus as claimed in claim 13, wherein the reinforcing matrix has an overlapping S design.

15. The apparatus as claimed in claim 13, wherein the flexible material is polyurethane.

16. The apparatus as claimed in claim 13, further comprising a series of deformable struts at a proximal end of the expandable cannula, the series of struts forming an expandable fluid outlet from the expandable cannula.

17. The apparatus as claimed in claim 16, wherein the impeller is located in the expandable fluid outlet.

18. The apparatus as claimed in claim 13, further comprising a series of deformable struts at a distal end of the expandable cannula, the series of struts being deformable to a first configuration to form an insertion tip for the elongated cannula.

19. The apparatus as claimed in claim 18, wherein the series of struts are positioned at an inlet of the expandable cannula for fluid moving across the impeller.

20. The apparatus as claimed in claim 18, wherein the series of struts is deformable to a second configuration to prevent obstructions from entering an open end of the expandable cannula.

21. The apparatus as claimed in claim 13, further comprising a first series of deformable struts adjacent a first open end of the tube of flexible material and a second series of deformable struts adjacent a second open end of the tube of flexible material.

22. The apparatus as claimed in claim 21, wherein in a first position of the reinforcing matrix, the first series of struts and the second series of struts, the expandable cannula has a first diameter, and in a second position of the reinforcing matrix, the first series of struts and the second series of struts, the expandable cannula has a diameter greater than the first diameter.

23. The apparatus as claimed in claim 21, wherein the first and second series of struts are connected to the reinforcing matrix.

24. The apparatus as claimed in claim 23, wherein the first series of struts and the second series of struts are formed integrally with the reinforcing matrix.

25. The apparatus as claimed in claim 21, wherein the first and second series of struts are formed of the same material.

26. The apparatus as claimed in claim 21, wherein the first and second series of struts are made of a shape memory material.

27. The apparatus as claimed in claim 21, wherein the first and second series of struts and the reinforcing matrix are formed from the same material.

28. The apparatus as claimed in claim 1, wherein the impeller includes an indentation in the hub proximate the proximal end of the blade.

29. A pump for pumping fluid at a desired location, the pump comprising:

a cannula having a compact state for insertion to the desired location and an expanded state;

an impeller positioned in the cannula and having a hub and a plurality of blades supported by the hub, each blade having a proximal end attached to the hub and a distal end, the blades being arranged in blade rows along the hub, the impeller having a stored configuration and a deployed configuration; and a drive mechanism for rotating the impeller in the deployed configuration, the blades in the stored configuration of the impeller being compressed so as to move the distal ends of the blades towards the hub, and the blades in the deployed configuration of the impeller extending away from the hub, the cannula being in the expanded state when the impeller is in the deployed configuration.

30. A method of pumping blood within a subject, the method comprising:

providing a blood pump including an expandable impeller having a plurality of staggered blades and an expandable cannula;

inserting the blood pump into the subject in a stored configuration;

positioning the blood pump so that the expandable impeller and expandable cannula are at a desired location;

expanding the expandable cannula and expanding the expandable impeller within the expandable cannula; and rotating the expanded impeller so that the impeller pumps blood through the expanded cannula.

\* \* \* \* \*